(12) United States Patent
Honda

(10) Patent No.: US 10,064,636 B2
(45) Date of Patent: Sep. 4, 2018

(54) METHOD FOR REMOVING CALCULUS FROM AN ACCESS SHEATH

(71) Applicant: Terumo Kabushiki Kaisha, Shibuya-ku, Tokyo (JP)

(72) Inventor: Kei Honda, Hadano (JP)

(73) Assignee: TERUMO KABUSHIKI KAISHA, Shibuya-Ku, Tokyo (JP)

( * ) Notice: Subject to any disclaimer, the term of this patent is extended or adjusted under 35 U.S.C. 154(b) by 612 days.

(21) Appl. No.: 14/674,508

(22) Filed: Mar. 31, 2015

(65) Prior Publication Data

US 2016/0287271 A1    Oct. 6, 2016

(51) Int. Cl.
| | | |
|---|---|---|
| *A61B 17/221* | (2006.01) | |
| *A61B 17/00* | (2006.01) | |
| *A61B 17/22* | (2006.01) | |
| *A61B 17/3203* | (2006.01) | |
| *A61B 17/32* | (2006.01) | |

(52) U.S. Cl.
CPC ...... *A61B 17/221* (2013.01); *A61B 17/00234* (2013.01); *A61B 17/22* (2013.01); *A61B 17/22032* (2013.01); *A61B 17/3203* (2013.01); *A61B 2017/003* (2013.01); *A61B 2017/00553* (2013.01); *A61B 2017/2215* (2013.01); *A61B 2017/22034* (2013.01); *A61B 2017/22039* (2013.01); *A61B 2017/22082* (2013.01); *A61B 2017/320012* (2013.01); *A61B 2217/007* (2013.01)

(58) Field of Classification Search
CPC . A61B 17/221; A61B 17/22031; A61B 17/22; A61B 2017/22034; A61B 1/307
See application file for complete search history.

(56) References Cited

U.S. PATENT DOCUMENTS

2005/0261705 A1* 11/2005 Gist ..................... A61B 17/221
                                                                606/113

OTHER PUBLICATIONS

U.S. Appl. No. 14/222,021, filed Mar. 21, 2014, Kei Honda.
U.S. Appl. No. 14/221,954, filed Mar. 21, 2014, Kei Honda.
U.S. Appl. No. 14/221,858, filed Mar. 21, 2014, Kei Honda.

* cited by examiner

*Primary Examiner* — Katherine Rodjom
(74) *Attorney, Agent, or Firm* — Buchanan Ingersoll & Rooney PC

(57) ABSTRACT

A method involves introducing a gathering part into a lumen in an ureteral access sheath in which is located calculus, wherein at least a part of the ureteral access sheath is located in an ureter in a living body. The gathering part is moved along the lumen in the ureteral access sheath in a forward direction toward the calculus, and then movement of the gathering part in the forward direction is stopped to position the gathering part adjacent the calculus so that the calculus is positioned between the distal end of the ureteral access sheath and the gathering part. The gathering part is expanded while the gathering part is positioned adjacent the calculus, and the calculus is then introduced into the gathering part.

18 Claims, 19 Drawing Sheets

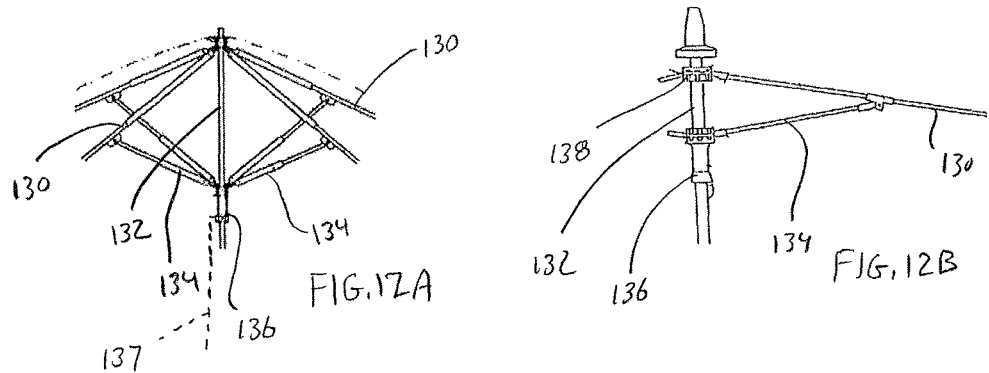
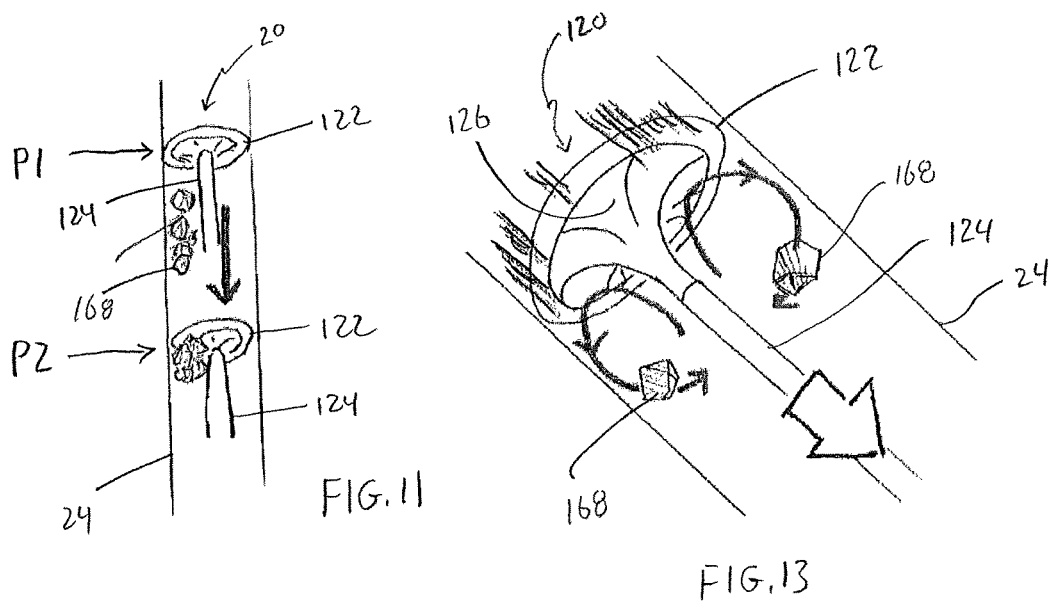

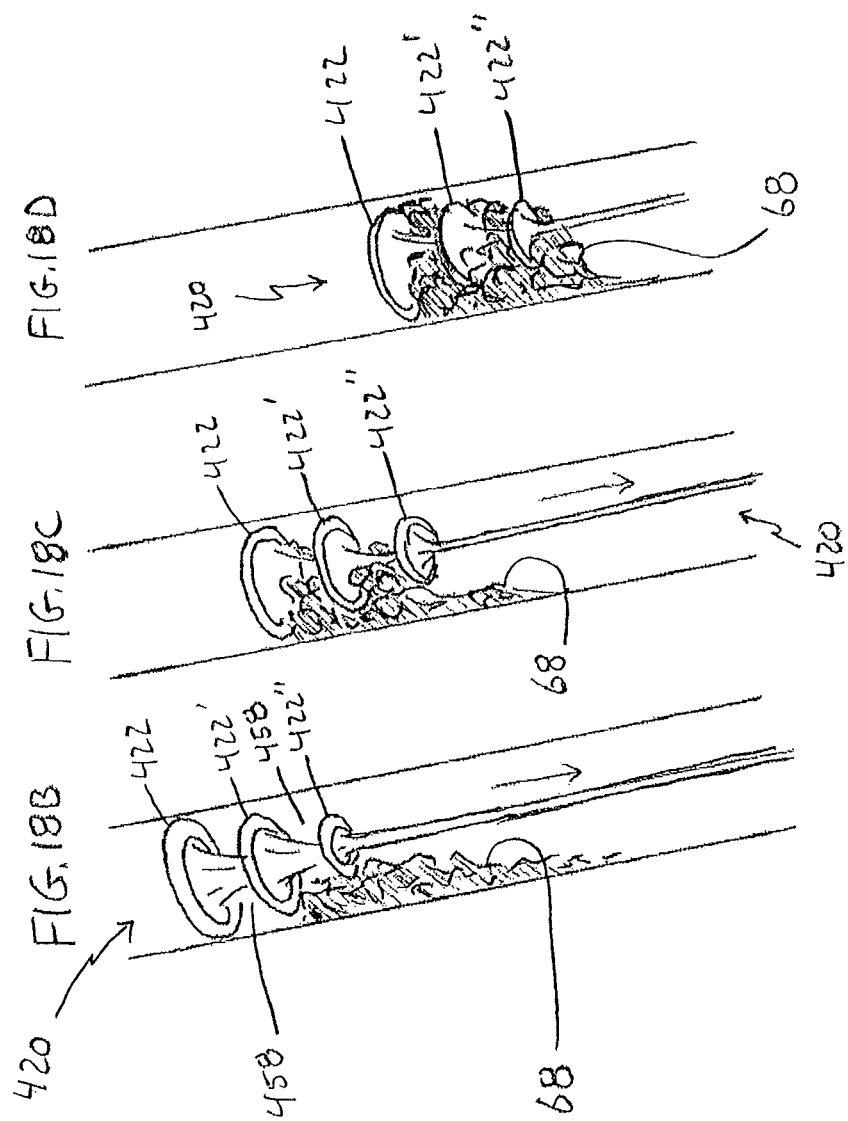

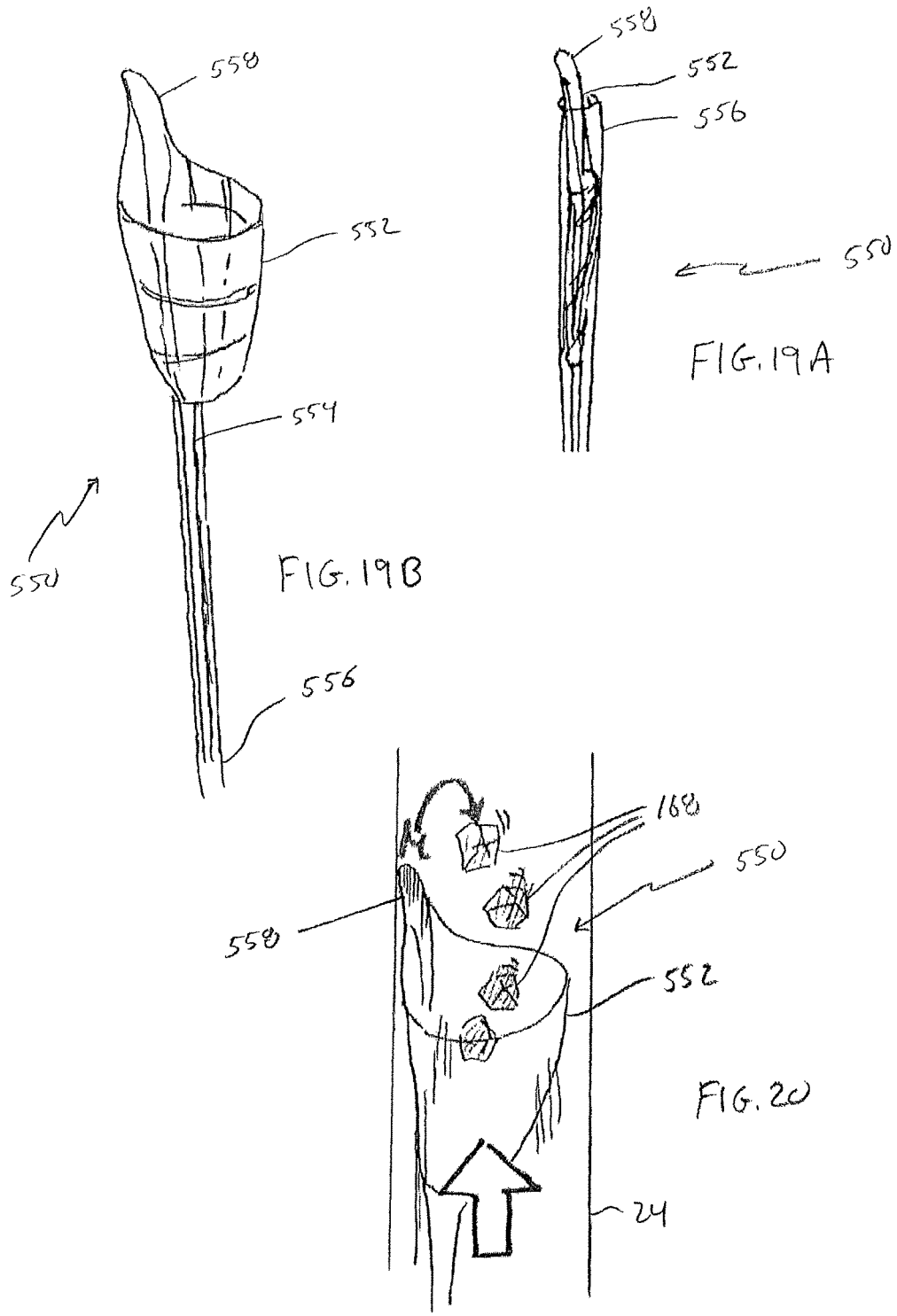

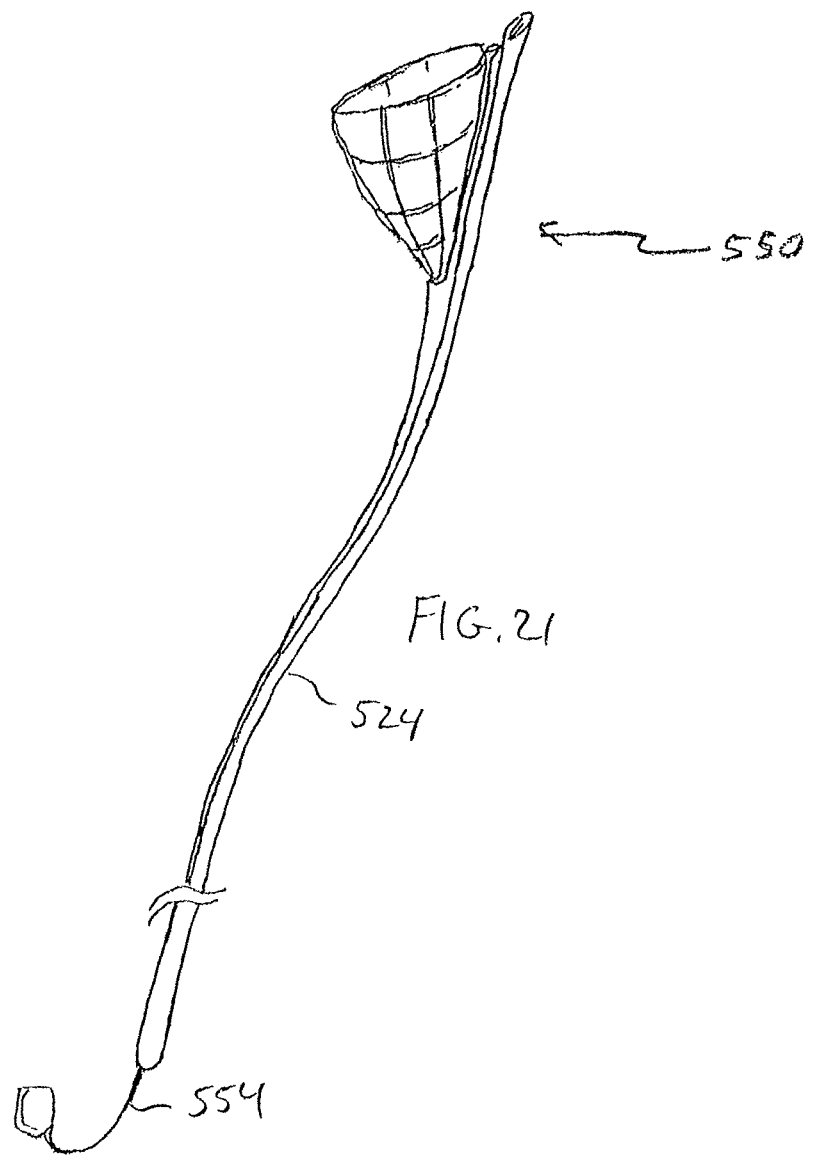

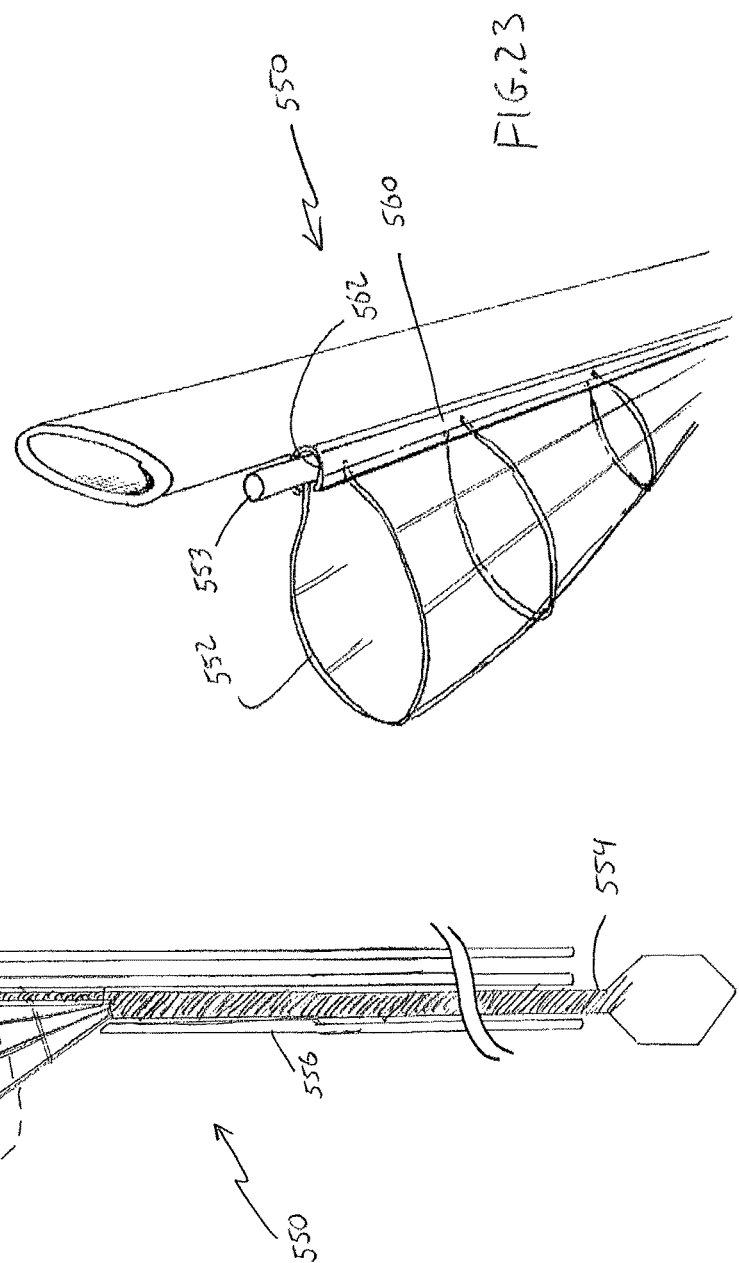

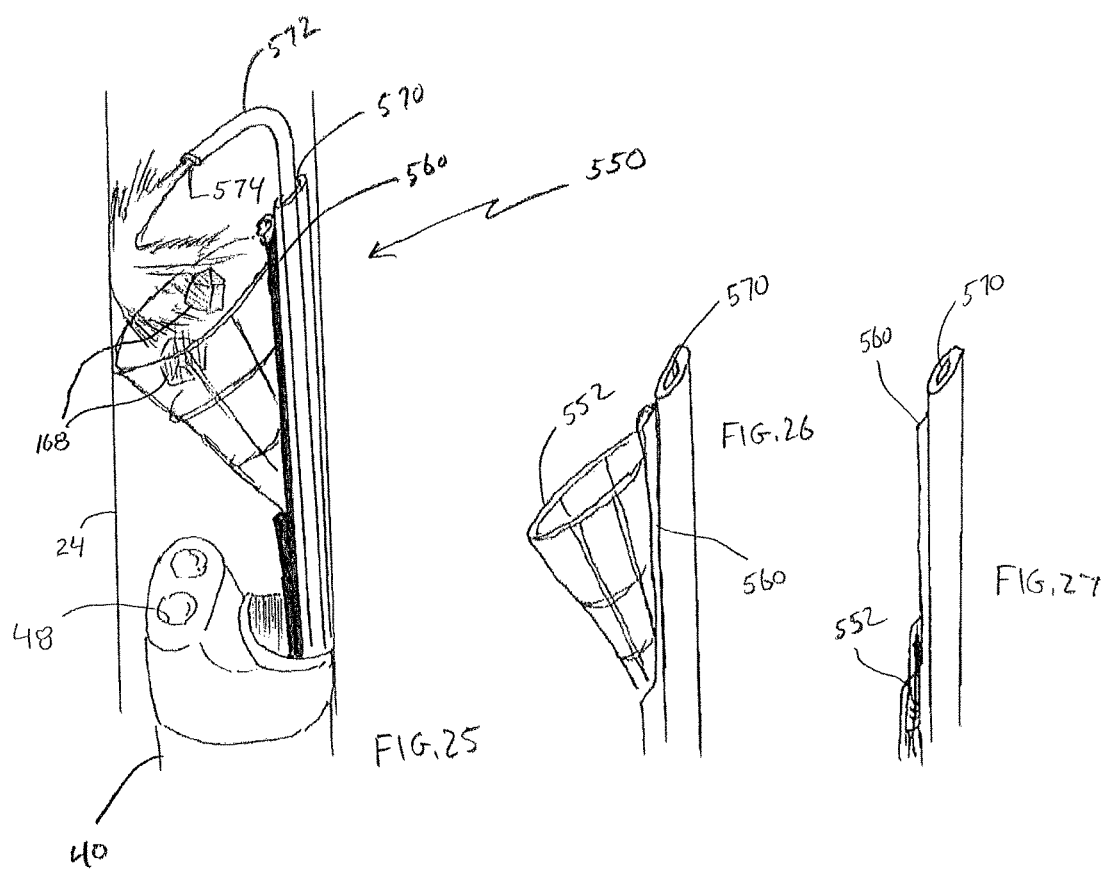

METHOD FOR REMOVING CALCULUS FROM AN ACCESS SHEATH

CROSS-REFERENCE TO OTHER APPLICATIONS

This application discloses subject matter related to subject matter described in U.S. application Ser. No. 14/222,021, U.S. application Ser. No. 14/221,954 and U.S. application Ser. No. 14/221,858, the entire content of each of which is incorporated herein by reference.

TECHNICAL FIELD

The present invention generally pertains to methods and systems for retrieving/removing a mass from a human body. More specifically, the invention involves methods and systems for retrieving/removing stone(s) (e.g., calculus or calculi) from a portion of a human body such as the renal pelvis or the ureter.

BACKGROUND DISCUSSION

The term urinary calculus (calculi) (e.g., kidney stone(s) and ureteral stone(s)) refers to mass(es) or stone(s), typically solid particle(s), that form in the human body and is located in the kidney and/or the ureter. They can exhibit a variety of chemical compositions including calcium oxalate, calcium phosphate, uric acid, cystine, and struvite.

Stone disease (e.g., kidney stones and ureteral stones) is a relatively common urological disorder. The presence of calculus in the body can manifest itself in a variety of ways and can produce a number of medical ailments. For example, the presence of calculus in the renal pelvis and/or the renal calix (i.e., the lumen of the kidney) can cause blood in the urine, urinary obstruction, infection, and various degrees of pain ranging from vague frank pain to much more severe pain not capable of being relieved through general pain medication. The presence of stones or calculi in the ureter can result in relatively severe side and back pain, pain below the ribs, and pain that sometimes spreads to the lower abdomen and groin, as well as pain during urination and hematuria.

Fortunately, many calculi or stones pass out of the body without requiring any specific medical intervention. In those situations where the calculus does not naturally pass out of the body, a medical procedure may be required. Known medical procedures typically fall into three categories.

In the past, three main treatments have been used to address calculus or kidney stones. These include shock wave lithotripsy (ESWL), transurethral lithotripsy or ureteroscopy (URS), and percutaneous nephrouretero lithotripsy (PCNL) which is sometimes also referred to as percutaneous nephrolithotomy (PCN).

Shock wave lithotripsy is performed as an extracorporeal treatment. This treatment utilizes a machine called a lithotripter that operates by directing ultrasonic or shock waves from outside the body, through the skin and tissue, and at the calculi or stones. Repeated shock waves apply stress to the stones, eventually breaking the individual stones into smaller pieces which can more easily pass through the urinary tract in urine. One benefit associated with shock wave lithotripsy is that it is a rather simple procedure. But it has been found that there is a relatively high rate of kidney stone recurrence following shock wave lithotripsy.

Transurethral lithotripsy or ureteroscopy represents one such alternative form of treatment. This treatment involves the use of small fiber optic instrument (endoscope) called an ureteroscope which allows access to the calculus in the ureter or kidney. The ureteroscope can be a rigid ureteroscope or more commonly, a flexible ureteroscope. The ureteroscope allows the medical professional to visualize the stone as the ureteroscope moves along the ureter or enters the kidney by way of the bladder and the urethra. Once the calculus is visualized, a basket-like device is used to grasp smaller stones and remove them. If the calculus is excessively large to remove as a single piece, it can be broken into a smaller pieces by using laser energy.

The third form of treatment is percutaneous nephrolithotomy. This procedure is often used with relatively larger calculus that cannot be effectively treated with either ESWL or URS. Percutaneous nephrolithotomy involves nephrostomy; making an incision at the appropriate location, needling by paracentesis needle, positioning a guide wire through the paracentesis needle's lumen into the kidney under radiographic guidance, and then expanding perforated site. A nephroscope is then moved into the kidney via nephrostomy to visualize the calculus. Fragmentation of the calculus can be performed using an ultrasonic probe or laser.

Though these procedures have been commonly used, they are susceptible of certain short comings. For example, the ESWL procedure results in a relative large number of small calculi or small stones, while other procedures require a relatively narrow and long access route or are difficult to implement due to the inability to accurately capture the stones. In addition to, many crush pieces should be removed one by one in URS and PCNL procedure. The procedure time can also be excessively long, and can result in a relatively low "stone free rate." The recurrence rate can also be unacceptably high. And the potential patient complications (e.g., ischemia of the ureter, obstruction of ureter, back-flow and/or high-stress to the renal pelvis, infection of the urinary tract, and other possible injury) can be undesirably high.

SUMMARY

One aspect of the disclosure here involves a method comprising removing from a lumen in an ureteral access sheath a calculus retrieving device used to retrieve calculus in a living body, wherein the living body includes a ureter extending between a bladder in the living body and a kidney in the living body, with at least a portion of the ureteral access sheath being located in the ureter, and the calculus retrieving device being removed from the lumen of the ureteral access sheath while the ureteral access sheath is positioned in the living body, with calculus being located in the lumen in the ureteral access sheath following removal of the calculus retrieving device from the ureteral access sheath. The method also involves introducing a gathering member into the lumen in the ureteral access sheath, moving the gathering member along the lumen in the ureteral access sheath in a forward direction toward the calculus so that the gathering member approaches the calculus, stopping the movement of the gathering member in the forward direction to position the gathering member between the proximal end of the ureteral access sheath and the calculus, expanding the gathering member while the gathering member is positioned between the proximal end of the ureteral access sheath and the calculus, wherein the expansion of the gathering member opens a gathering part of the gathering member so that the gathering part is open to receive the calculus. The method also includes introducing the calculus into the open gathering part of the gathering member, moving the gathering member with the calculus enclosed in the gathering part of the gathering member along the lumen in the ureteral access sheath in a direction toward the bladder, and removing the gathering member as well as the calculus enclosed in the gathering part of the gathering member from the lumen of the ureteral access sheath.

In accordance with another aspect, a method involves introducing a gathering part into a lumen in an ureteral access sheath in which is located calculus, where the gathering part is introduced into the ureteral access sheath while at least a part of the ureteral access sheath is located in an ureter in a living body, and where the gathering part is expandable to an open state in which the gathering part is open to receive the calculus. The method also involves moving the gathering part along the lumen in the ureteral access sheath in a forward direction toward the calculus in the lumen of the ureteral access sheath and toward a distal end of the ureteral access sheath, stopping movement of the gathering part in the forward direction in the lumen of the ureteral access sheath to position the gathering part adjacent the calculus so that the calculus is positioned between the distal end of the ureteral access sheath and the gathering part, expanding the gathering part, while the gathering part is positioned adjacent the calculus, to the open state in which the gathering part is open to receive the calculus, introducing the calculus into the receiving part of the gathering member, and removing the gathering part as well as the calculus in the gathering part from the lumen of the ureteral access sheath.

Other features and aspects of the methods disclosed here will become more apparent from the following detailed description considered with reference to the accompanying drawing figures in which like elements are designated by like reference numerals.

BRIEF DESCRIPTION OF DRAWINGS

FIG. 11 is a schematic illustration of the raking member positioned in an ureteral access sheath and movable between two positions.

FIG. 12A is a perspective view of an example of structural aspects of the raking part and FIG. 12B is an enlarged view of a portion of the raking part depicted in FIG. 12A.

FIG. 13 is a perspective view of the raking member positioned in the ureteral access sheath illustrating operation aspects of the raking member.

FIGS. 18A-18D are perspective views of another embodiment of the raking member positioned in an ureteral access sheath.

FIG. 19A is a perspective view of gathering member with a gathering part in the closed or contracted state, and FIG. 19B is a perspective view of the gathering member with the gathering part in the open or expanded state.

FIG. 20 is a perspective view of the gathering member positioned in the ureteral access sheath and illustrating operation aspects of the gathering member.

FIG. 21 is a perspective view of the gathering member.

FIG. 22 is a side view of the gathering member provided with a lumen for an irrigation tube.

FIG. 23 is an enlarged view of the portion of the gathering member in FIG. 22 circled by a dotted outline.

FIG. 25 is a perspective view of the gathering member positioned in the ureteral access sheath illustrating operation aspects of the gathering member.

FIG. 26 is a perspective view of the gathering member with the gathering part in the open or expanded state.

FIG. 27 is a perspective view of the gathering member with the gathering part in the closed or contracted state.

DETAILED DESCRIPTION

Set forth below is a detailed description of features and aspects of the retrieving system, device and operational procedure or method described here as examples of the disclosed invention. The systems, devices and operational procedures disclosed here for retrieving calculus have useful application to retrieve calculus/calculi located in the living body, including calculus/calculi located in the kidneys (kidney stones). The references below to calculus should be understood to refer to calculus in the singular as well as calculi in the plural. It is also to be understood that the methods, systems and devices disclosed here are not limited to retrieving calculus in a living body. Calculus as used here naturally includes stones (calculus) of various sizes, inclusive of calculus fragments generated by the lithotripsy.

Generally speaking, the calculus retrieving device disclosed here, as represented by the several embodiments representing examples of the inventive retrieving device (and method), is configured to be positioned inside a living body at a position which will allow the retrieving device to suck-in or draw-in calculus to be retrieved. Set forth below is a detailed description of features and aspects of the calculus retrieving system, including a calculus retrieving device, and method described here by way of various embodiments representing examples of the disclosed inventions. The systems, devices and methods or operational procedures disclosed here for retrieving calculus have particular useful application to retrieve calculus located at places in the human body where removal of the calculus may otherwise be difficult due to, for example, the need to traverse a rather sharp curve to access the target site and/or the need to enter a rather narrow region to move toward and reach the target site.

Generally speaking, the calculus retrieving device disclosed here, as characterized by the several embodiments representing examples of the inventive calculus retrieving device (and method), is configured to be positioned inside a living body, at a position adjacent the location of calculus to be retrieved from the living body. The calculus (stone/stones) is drawn towards the retrieving device by creating a suction force in the retrieving device. After the calculus is retrieved, the calculus is retained or held by the retrieving device. The retrieving device can then be moved to the new location in the living body at which the retrieved calculus is to be repositioned. The retained calculus is subsequently released at the new location in the living body. Appropriate procedures (e.g., lithotripsy) can then be performed with respect to the calculus which has been moved. Alternatively, the retained calculus can be subsequently removed from the living body.

Figure 1:
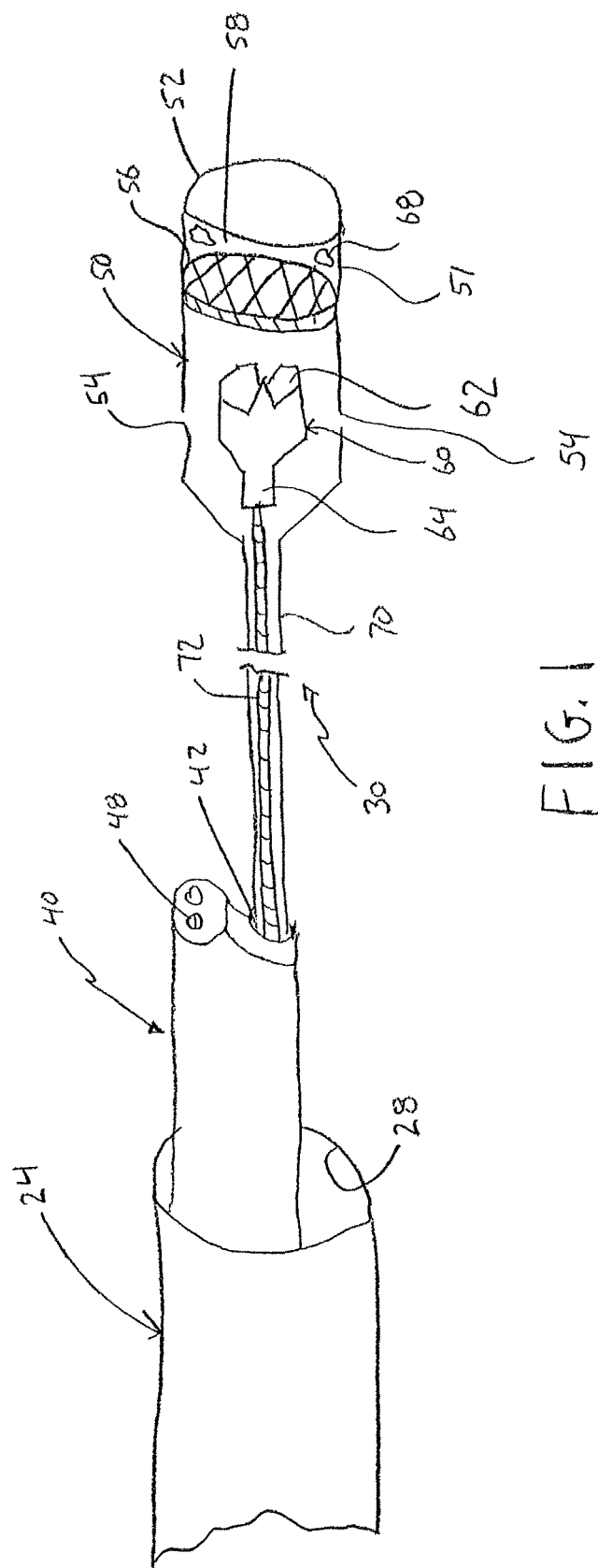
FIG. 1 is a schematic illustration of a system useful to retrieve calculus/calculi, including a retrieving device connected to an operation member (not shown in FIG. 1) through the intermediary of a lumen in an elongated body.

Turning now to the drawing figures, FIG. 1 illustrates, in a schematic fashion, a system 20 for retrieving and moving (removing) calculus (stone or stones) located in a living body. The system 20 includes a retrieving device 30 and an elongated body 40 possessing a lumen to deliver the retrieving device 30 to the desired place in the living body. In this illustrated embodiment representing one example of the system disclosed here, the elongated body 40 is an endoscope, particularly an ureteroscope. The endoscope or ureteroscope 40 includes a lumen or instrument channel 42, which receives a portion of the retrieving device 30, as will be described in more detail below. During use of the retrieving device 30, the endoscope 40 is introduced into the living body by way of a ureteral access sheath 24. That is, the ureteral access sheath 24 is located in a lumen in the living body, and the endoscope 40 is introduced into and passes through a lumen 28 in the ureteral access sheath 24.

Figure 3:
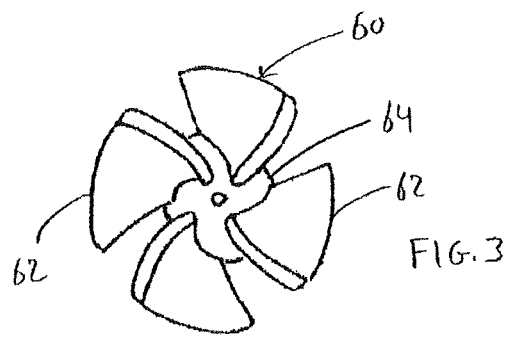
FIG. 3 is a front view of the impeller forming a part of the retrieving device shown in FIG. 2.
Figure 2:
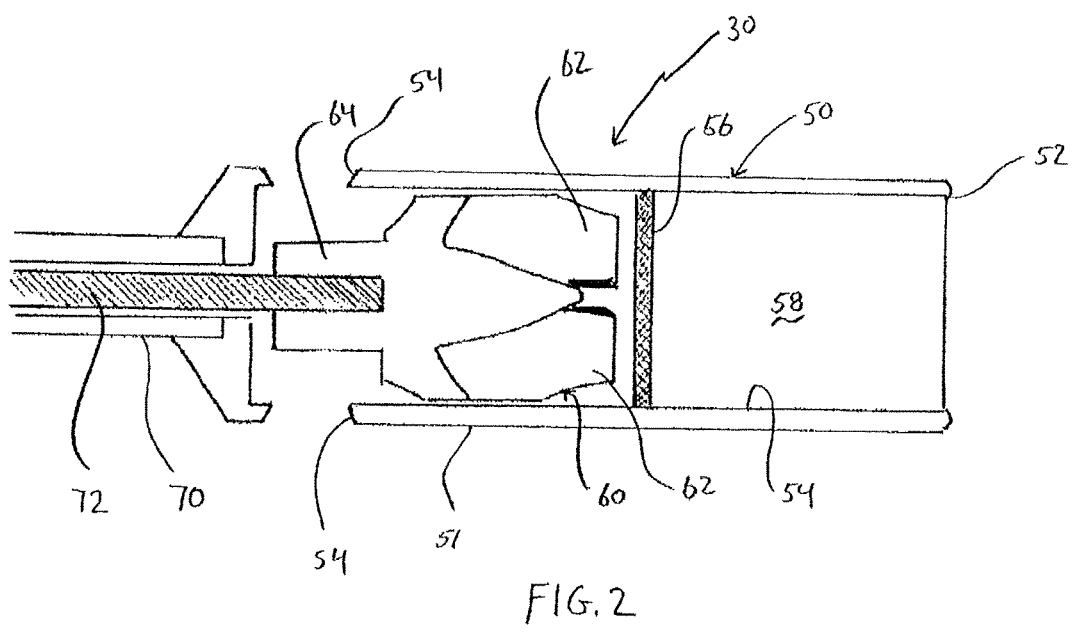
FIG. 2 is a side view, partially in cross section, of a retrieving device according to an embodiment representing an example of the retrieving device disclosed here.

Additional details and features associated with the calculus retrieving device 30 can be seen with reference to FIGS. 1, 2 and 3. The calculus retrieving device 30 includes a suction head 50 comprised of an elongated body or housing 51 having an open distal end 52. The housing 51 is a tubular housing possessing a lumen 55 defining an interior of the housing 51. The housing 51 can be configured as a cylindrical elongated body or housing.

The retrieving device 30 also includes a rotatable suction-producing part located inside the housing 51. In the illustrated embodiment, the rotatable suction-producing part is in the form of an impeller 60. As shown in FIGS. 1 and 2, the impeller is positioned in the housing 51 at a location spaced away from (i.e., proximally or rearwardly) the open distal end 52. An example of the impeller 60 is illustrated in FIG. 3. The impeller 60 includes a plurality of circumferentially spaced apart fins or blades 62 that are fixed to a central hub 64. The fins or blades 62 of the impeller 60 may be twisted fins or blades. The hub 64 is fixed or connected to a rotatably driven shaft 72 forming part of the device so that the shaft 72 and the impeller 60 rotate together as a unit. The impeller 60 is configured so that rotation of the impeller 60 in one rotational direction produces suction in the lumen 55 (in the interior) of the housing 51, while rotation of the impeller 60 in the opposite rotational direction produces the opposite result, namely an outwardly directed force out of the lumen 55. The blades 62 of the impeller 60 shown in FIGS. 2 and 3 are preferably twisted from the distal tip of the blades 62 (radially outermost tip of the blades) toward the bottom portion of the impeller where the blades are mounted. When the direction of the impeller rotation is the same as the twist direction of the blades 62, a suction force is generated. This direction of rotation of the impeller is referred to as overspin direction.

The drive shaft 72 that is connected to the hub 64 of the impeller 60 is positioned inside a shaft cover 70 and is covered by the shaft cover 70 which forms part of the device. In the illustrated embodiment, the drive shaft 72 is completely covered by the shaft cover 70. The shaft cover 70 is fixed to the housing 51 forming the suction head 50 so that movement of the shaft cover 70 results in movement of the suction head 50 (including the housing 51 and the impeller 60).

The housing 51 forming the suction head 50 includes a plurality of circumferentially spaced apart openings or through holes 54. These openings or through holes 54 are positioned closer to the proximal end of the housing 51 than the distal end of the housing 51. These openings or through holes 54 form outlets (an exhaust path) during operation of the retrieving device, as will become more apparent from the description below. That is, liquid (e.g., water) which has been drawn into the housing 51 of the suction head 50 during operation of the retrieving device 30 is exhausted or discharged out of the suction head 50 by way of the outlets 54.

The suction head 50 further includes a filter 56 located inside the housing 51 at a position between the distal end of the impeller 60 and the open distal end 52 of the suction head 50. This filter 56 is a disc-shaped mesh member that allows the passage of fluid (e.g., liquid such as water), while also preventing the passage of calculus which has been retrieved through operation of the retrieving device 30. The filter 56 possesses an outer periphery (outer circumferential surface) in contact with the inner periphery of the suction head 50. The filter 56 is positionally fixed within the interior of the housing 51 forming the suction head 50.

The suction head 50 also includes a retrieval space 58 located between the filter 56 and the open distal end 52 of the housing 51. As will be described in more detail below, this retrieval space 58 is configured to receive calculus which has been retrieved as a result of the operation of the retrieving device 30.

During operation of the retrieving device 30, the suction head 50 is located at a position in a living body (a lumen in a living body) to retrieve calculus. That is, the suction head 50 is positioned relative to the calculus to be retrieved such that during operation of the retrieving device 30, the calculus will be drawn towards (sucked towards) the suction head 50. When the suction head 50 is properly positioned relative to the calculus to be retrieved, the impeller 60 is rotatably driven through operation of a drive device connected to the drive shaft 72. The drive device rotates the drive shaft 72, which in turn rotates the impeller 60. The impeller 60 is rotatably driven in a direction to create suction in the interior of the housing 51 that draws calculus toward the open distal end 52 of the suction head 50. The suction force created by the rotation of the impeller 60 draws relatively smaller calculus (schematically shown in FIG. 1 and identified as 68) through the open distal end 52 of the suction head and into the retrieval space 58 in the housing 51. The suction force created by the rotation of the impeller 60 can also draws relatively larger calculus into contact with the distal end of the suction head 50. That is, calculus possessing an outer dimension larger than the size of the open distal end 52 of the suction head 50 can nevertheless be drawn towards the suction head 50 and retained by the suction head 50 by creating sufficient suction force in the interior of the housing 51 that holds the relatively larger calculus in contact with the distal end of the suction head 50.

Thus, by positioning the suction head 50 in the living body so that the open distal end 52 of the suction head 50 is located at a position that will allow the calculus (i.e., calculus to be retrieved) to be drawn-into or sucked into the retrieval space 58 upon rotational operation of the impeller 60, it is possible to retrieve calculus and hold the retrieved calculus either in the retrieval space 58 or at the distal end of the suction head 50. As the impeller 60 is rotated to draw calculus toward the suction head 50, liquid (e.g., water) is drawn into the retrieval space 58 by way of the distal open end 52 of the suction head 50. This liquid is passes through the filter 56, and is exhausted or discharged outside the housing 51 of the suction head 50 through the openings or through holes 54. On the other hand, the filter 56 is sized to ensure that calculus which is drawn into the retrieval space 58 of the suction head 50, does not pass through the filter 56. The rotational operation of the impeller 60 thus causes liquid flow in which liquid enters the distal open end 52 of the suction head 50, passes through the filter 56, and exits through the through holes or openings 54 in the suction head 50. Depending upon operation of the impeller 60, the liquid exhausted through the openings or through holes 54 can also be at least partially drawn back into the interior of the suction head 50, thus creating a rather turbulent and continuous liquid cycle in which the same liquid is repeatedly drawn into the suction head, exhausted through the suction head 50, drawn into the suction head, etc. This turbulent and continuous liquid cycle can help facilitate retrieval of calculus in the retrieval space 58 of the suction head 50. This is because the suction force per rotation of the impeller is increased. In addition, the calculus tends to float, making it easier to draw-in or retrieve the calculus. When drawing-in calculus in a narrow lumen in a living body (e.g. ureter), the continuous liquid cycle helps prevent fluid surrounding calculus from drying up.

Set forth next is a description of ways in which the system for retrieving calculus disclosed here can be used, as well as a description of operational procedures performed using the calculus retrieving system. Calculus that is not excessively large can be retrieved and removed from the living body using the retrieving system, device and operational procedures or methods disclosed here. But it is sometimes necessary or desirable to break-up calculus located in a living body. For instance, if the calculus is relatively large (e.g., larger than the ureter diameter), it is not possible to remove the calculus from the living body. In such situations, it would be desirable to break-up the calculus into smaller size pieces. This can oftentimes be accomplished using lithotripsy. Circumstances may make it difficult to perform lithotripsy to break-up calculus in the living body. For example, the calculus may be located at a place where damaged tissue exists, for example in a portion of the ureter in which there is damaged tissue. Alternatively, the calculus may be located in a portion of the living body (e.g., ureter) that is rather small in size (i.e., a narrow space) and difficult to access with appropriate instrumentation and equipment for performing lithotripsy (e.g., a lower calix). The retrieving system and retrieving device disclosed here can be used to retrieve calculus, move the retrieved calculus to a new (different) location which presents a larger space (e.g., the kidney or an upper calix) to perform lithotripsy or which presents a region where there is normal (non-damaged tissue) tissue.

Figure 4:
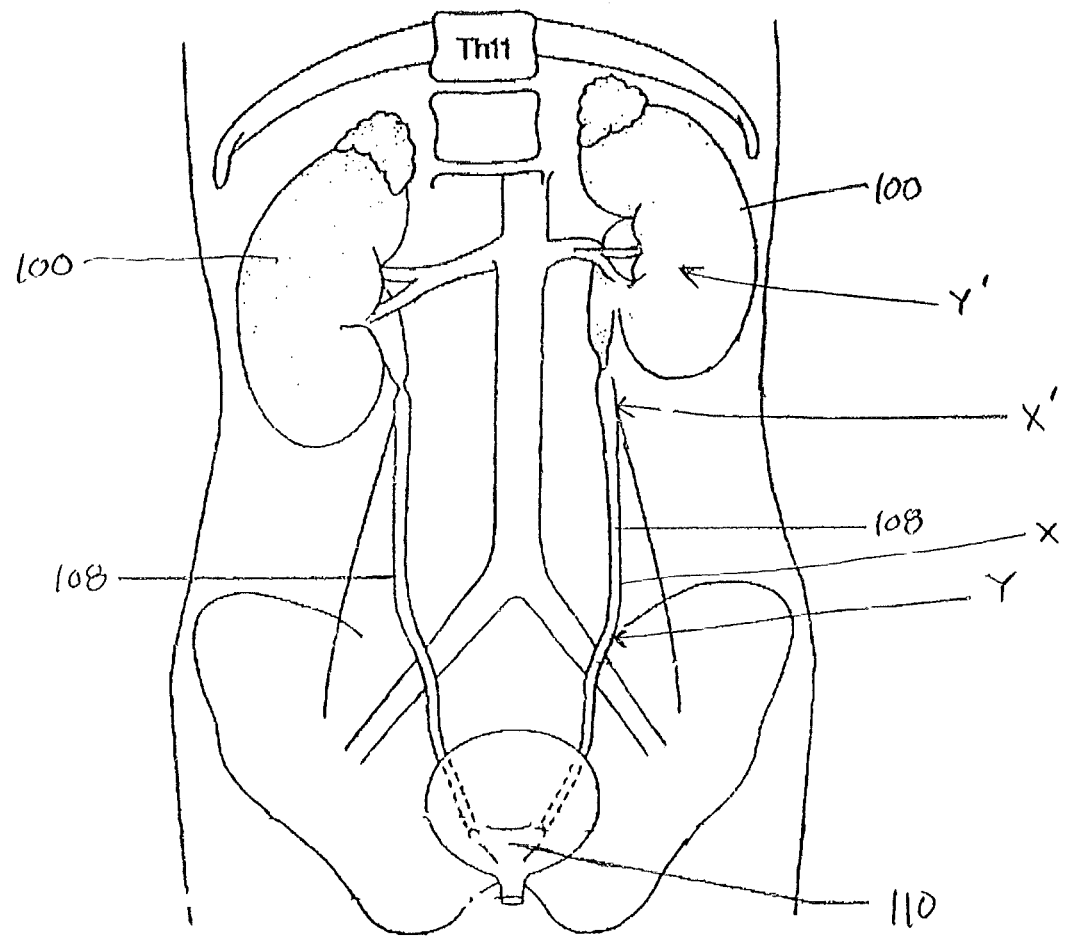
FIG. 4 is a schematic illustration of a portion of the human anatomy, including the urinary tract.
Figure 5:
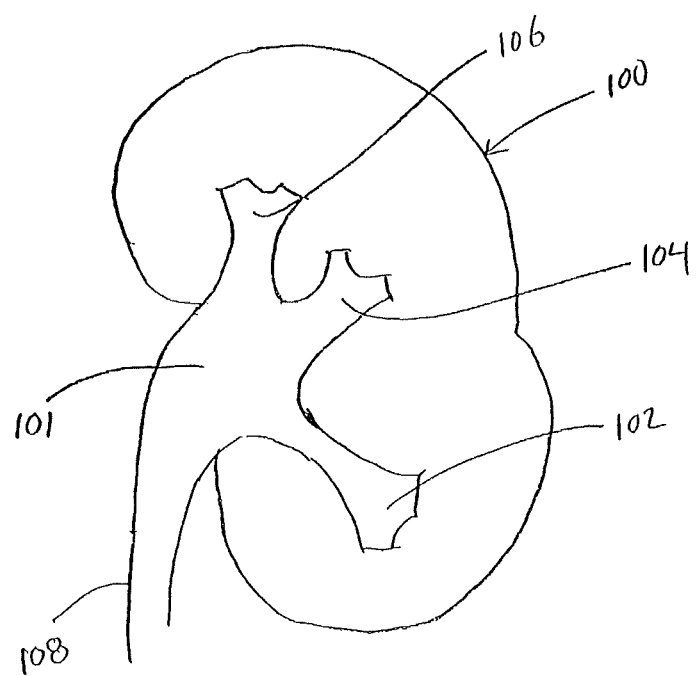
FIG. 5 is a schematic illustration of a human kidney, illustrating the renal pelvis, a lower calix (lower renal calix), a middle or intermediate calix (middle or intermediate renal calix), and an upper calix (upper renal calix).

As explained, the retrieving device and system disclosed here can be used to retrieve calculus from a living body and remove the retrieved calculus from the living body. The calculus which is to be retrieved by the retrieving system disclosed here can be calculus located at any place that is accessible by the retrieving system disclosed here. Referring to FIG. 5, examples include calculus located in the ureter 108, calculus located in the renal pelvis 101, calculus located in one of the calices 102, 104, 106, etc. The retrieving device and system disclosed here can also be used to retrieve calculus from one place in the living body, move the retrieved calculus to a new (different) place in the living body where, for example, lithotripsy can be more easily performed to break-up the calculus, and then release the retrieved and moved calculus at the new location. By way of example, and with reference to FIG. 4, it is possible to retrieve calculus at the location X in the ureter (representing an example of a region of narrow size or damaged tissue) and move the retrieved calculus to the position X' in the ureter (representing an example of a region of larger size or normal non-damaged tissue). It is also possible to retrieve calculus at the location Y (representing an example of a region of narrow size or damaged tissue) and move the retrieved calculus to the position Y' in the kidney (representing another example of a region of larger size or normal non-damaged tissue).

Figure 6:
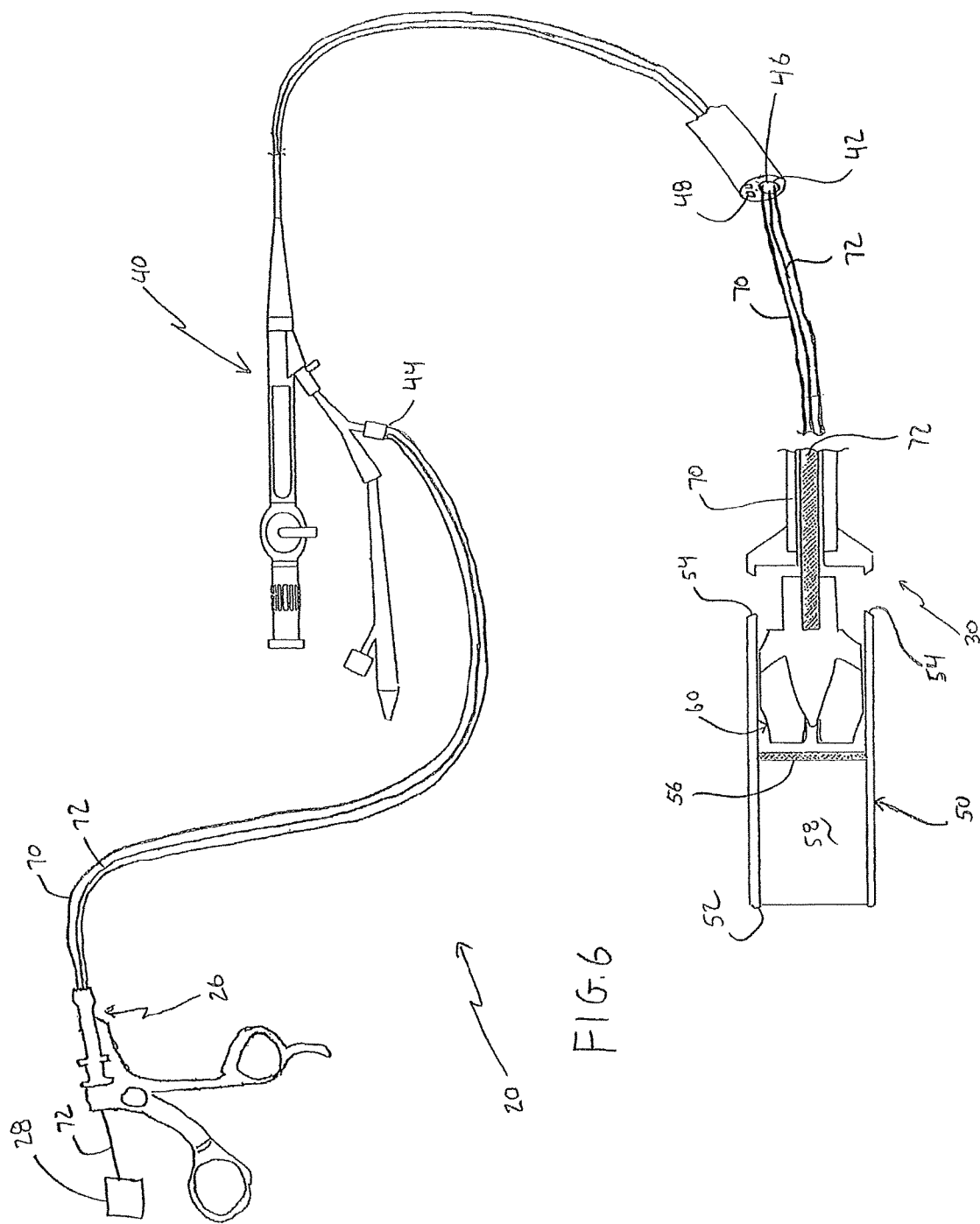
FIG. 6 is a schematic illustration of the retrieving system, including the retrieving device connected to the operation member through the intermediary of an elongated body such as an endoscope (ureteroscope).

To retrieve and remove/move the calculus, a retrieving system such as the retrieving system 20 shown in FIG. 6 can be used. Specifically, the calculus retrieving device 30 is used, together with the operating member 26 and the endoscope 40 (ureteroscope). The operating member 26 is connected to the shaft cover 70, so that operation of the operating member 26 causes the shaft cover 70 to move. That is, the operation of the operating member 26 causes the shaft cover 70 to axially move, which in turn causes the suction head 50 (including the impeller 60 and the filter 56) to also axially move. FIG. 6 schematically illustrates that the shaft 72 positioned within and extending along the axial length of the shaft cover 70 is connected to a driving device 28 (e.g., a geared motor). Operation of the driving device 28 rotates the shaft 72, which in turn rotates the impeller 60 positioned in the housing 51 of the suction head 50 of the calculus retrieving device 30. As shown in FIG. 6, the shaft cover 70 and the shaft 72 extend from the operating member 26, enter an inlet 44 of the instrument channel 42 in the ureteroscope 40, pass through the ureteroscope 40, and exit at an outlet at the distal end portion 46 of the ureteroscope 40.

In use, the shaft cover 70 is connected to the housing 51 of the suction head 50, and the proximal end of the shaft cover 70 and the shaft 72 are inserted into the outlet of the instrument channel 42 at the distal end portion 46 of the ureteroscope 40. The shaft cover 70 and the shaft 72 are pushed through the lumen (instrument channel 42) in the ureteroscope 40 until the proximal end of the shaft cover 70 and the proximal end of the shaft 72 exit out of the inlet 44 of the ureteroscope. The proximal end of the shaft 72 is then connected to the driving device 28, while the proximal end of the shaft cover 70 is fixed to the operating member 26.

In the case of the endoscope 40 being an ureteroscope, the ureteroscope is preferably a flexible ureteroscope. The ureteroscope 40 includes a viewing system that includes an objective lens or camera 48 schematically illustrated in FIG. 1 (and FIG. 16). In a known manner, this provides a field of view for the user or operator to facilitate carrying out the procedure involving locating calculus, retrieving the calculus, moving the calculus to the new location and releasing the calculus at the new location.

The description above explains that the retrieval of calculus using the retrieving system 30 disclosed here by way of example involves introducing the ureteral access sheath 24 into the lumen in the living body to position the ureteral access sheath 24 at the desired location in the lumen in the living body while the proximal end of the ureteral access sheath 24 remains outside the living body, introducing the retrieval system 30 into the instrument channel 42 in the endoscope 40 (i.e., inserting the proximal end of the drive shaft 72/shaft cover 70 into the outlet end of the instrument channel at the distal end of the endoscope 40 (ureteroscope) and advancing the drive shaft 72/shaft cover 70 along the instrument channel 42 toward the proximal end of the instrument channel until the drive shaft 72/shaft cover 70 are located outside of, and proximally beyond the proximal end of, the instrument channel 42), introducing the endoscope 40 (with the suction head 50 and the drive shaft 72/shaft cover 70) into the ureteral access sheath 24 that is positioned in the lumen of the living body (the endoscope 40 is introduced into the proximal end of the ureteral access sheath 24, which proximal end of the ureteral access sheath 24 is positioned outside the living body), advancing the endoscope 40 (with the suction head 50 and the drive shaft 72/shaft cover 70) along the ureteral access sheath 24 and to the location in the lumen in the living body at which is located the calculus to be retrieved. When the calculus is retrieved, the retrieval system is moved into the ureteral access sheath 24, and the retrieval system 30 is either removed from the living body or is moved to another location in the living body.

The operational procedure described above is utilized at least in part because the suction head 50 forming a part of the retrieval device 30 may be too large to introduce into and move along the instrument channel 42 of the endoscope 40.

It is possible that calculus (calculus fragments) may become deposited in the interior of the ureteral access sheath 24, and the presence of calculus in the ureteral access sheath 24 can present problems. For example, as the endoscope 40 is moved back and forth within the ureteral access sheath 24, calculus in the ureteral access sheath 24 can damage the endoscope 40.

Figure 8:
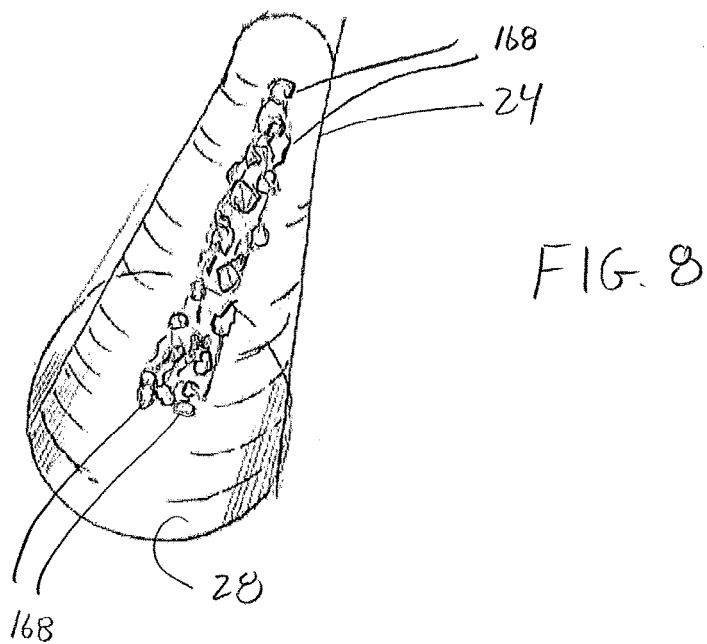
FIG. 8 is a schematic illustration of an ureteral access sheath illustrating calculus in the ureteral access sheath following operational procedures implemented to retrieve and move or remove calculus from a living body.

As described above in the description of the retrieval device 30 illustrated in FIGS. 1, 2 and 6, the suction head 50 is utilized to draw calculus into the interior of the housing of the suction head 50. The suction head 50 is moved along the ureteral access sheath 24 to the desired location for retrieving calculus. After the calculus is drawn into the housing of the suction head 50, the suction head 50 is pulled rearwardly or drawn back into the ureteral access sheath 24 and ultimately removed from the living body or moved to another location in the living body by moving the ureteroscope in which the suction head is mounted. As the suction head 50 moves or is pulled in the rearward direction along the ureteral access sheath 24, calculus that have been retrieved in the housing of the suction head may tend to fall out of the housing of the suction head and become deposited on the inner surface 28 of the ureteral access sheath 24 as illustrated in FIG. 8. In addition, calculus (especially small sized calculus such as fragments of calculus generated by lithotripsy) tend to flow into the ureteral access sheath as shown in FIG. 8 by virtue of fluid flow. This fluid flow can be urinary flow and can also result from taking the endoscope in and out of the ureteral access sheath 24.

Figure 9:
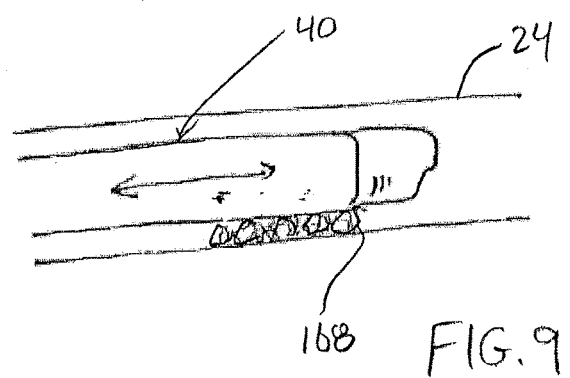
FIG. 9 is a schematic side view of the ureteral access sheath in which are located calculus and an endoscope.

Calculus in the interior (lumen) of the ureteral access sheath 24 can damage the endoscope as the endoscope moves back and forth within the ureteral access sheath 24. An example of this potential damage is illustrated in FIG. 9 which shows the endoscope 40 movable back and forth within the ureteral access sheath 24, as indicated by the arrow, and during this back and forth movement the endoscope 24 is in contact with the calculus 168 in the lumen of the ureteral access sheath 24. In addition, the lithotripsy procedure results in a relative large number of small fragments of calculus, and these small-sized fragments have the ability (sufficient size) to damage the endoscope 40. Such calculus fragments can be deposited rather easily in the interior of the ureteral access sheath 24, but are difficult to remove from the interior of the ureteral access sheath 24 by the retrieving procedure in existence.

Set forth below is a description of various ways in which calculus can be removed from the ureteral access sheath 24 to reduce the likelihood of damage to the endoscope 40.

Figure 7:
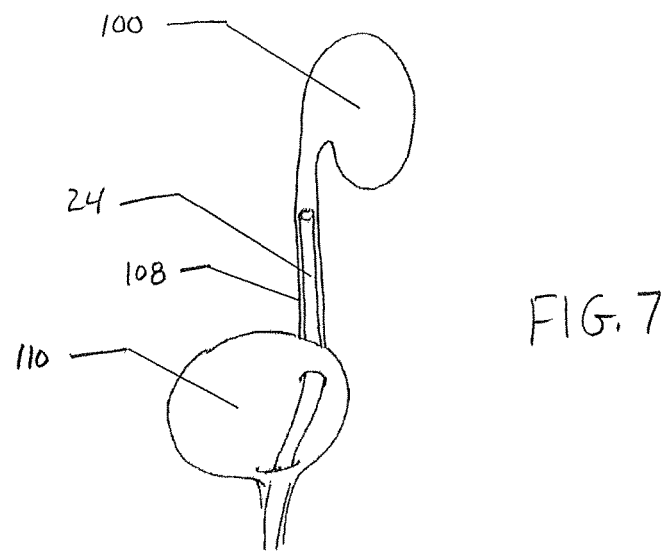
FIG. 7 is a schematic illustration of a portion of human anatomy including the kidney connected to the bladder by the ureter.

Before turning to the details of the various embodiments for removing calculus from the ureteral access sheath 24, reference is made to FIG. 7 which schematically illustrates the ureter 108 connecting the bladder 110 to the kidney 100. FIG. 7 also schematically illustrates the ureteral access sheath 24 positioned in a lumen in the living body. As illustrated by way of example, the access sheath 24 passes through the bladder 110, and at least the distal portion of the ureteral access sheath 24 is located in the ureter 108. It is of course to be understood that that the ureteral access sheath 24 may be positioned closer to or in the kidney 100, or spaced farther from the kidney 100, than that illustrated in FIG. 7. The illustration in FIG. 7 is simply intended to show a location for the ureteral access sheath 24 during the usage described above.

Figure 10A:
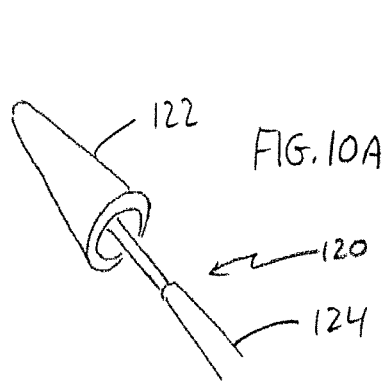
FIG. 10A is a perspective view of a raking member with a raking part in a closed or collapsed state.
Figure 10B:
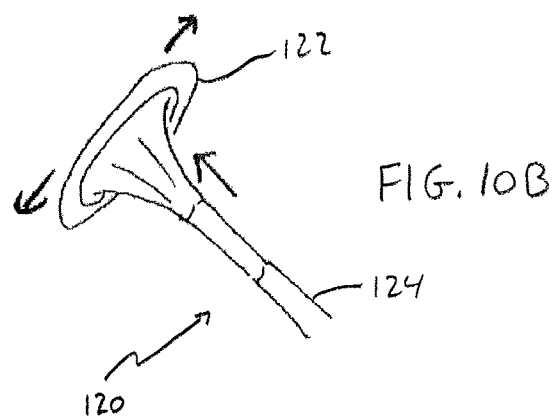
FIG. 10B is a perspective view of the raking member with the raking part in an open or expanded state.

One method or operational procedure for removing calculus from the interior (lumen) of the ureteral access sheath 24 is illustrated in FIGS. 10A, 10B, 11, 12A, 12B, 13 and 14. One embodiment of the method or operational procedure utilizes a raking member 120 illustrated in FIGS. 10A and 10B. The raking member 120 includes an elongated shaft 24 possessing a distal end connected to an expandable and collapsible raking part 122. FIG. 10A illustrates the raking member 120 in a first state or collapsed state in which the raking part 122 is closed or collapsed, whereas FIG. 10B illustrates the raking member 120 in a second state or expanded state in which the raking part 122 is open or expanded. In the open or expanded condition of the raking member 120, the raking part 122 is enlarged relative to the raking part 122 when the raking member 120 is in the closed or collapsed state shown in FIG. 10A.

One possible operational procedure involving the raking member 120 is as follows. The raking member 120 in the closed state shown in FIG. 10A is positioned in the instrument channel of the endoscope 40 (ureteroscope). The endoscope 40 together with the raking member 120 is then advanced in the forward direction to introduce the endoscope 40 together with the raking member 120 into the ureteral access sheath 24. The endoscope 40 together with the raking member 120 is then moved along the lumen in the ureteral access sheath 24 to approach the calculus in the ureteral access sheath 24 to be removed. The forward movement of the endoscope 40 is stopped in advance of the calculus. Another procedure involves introducing the endoscope 40 (ureteroscope) into the ureteral access sheath 24 while the ureteral access sheath 24 is positioned in the lumen of the living body, and introducing the raking member 120 (in the closed state) into the instrument channel 42 of the endoscope 40 while the endoscope 40 is in the ureteral access sheath 24. The raking member 120 in the closed state is then advanced along the instrument channel 42 so that the raking member 120 in the closed state enters the ureteral access sheath 24. The forward movement of the endoscope 40 is stopped in advance of the calculus.

The raking member 120 is then moved along the instrument channel 42 of the endoscope 40 and is introduced into the ureteral access sheath 24. The raking member 120 continues to be moved in the forward direction (toward the kidney) within the lumen of the ureteral access sheath 24 so that the raking member 120 approaches the calculus 168 in the lumen of the ureteral access sheath 24. Throughout this axial forward movement, the raking member 120 is kept in the closed state shown in FIG. 10A. The axial forward movement of the raking member 120 in the ureteral access sheath 24 continues until the raking member 120 in the closed state moves past, or is located beyond, the calculus 168 in the ureteral access sheath 24. After the raking member 120 in the closed state passes the calculus 168 in the ureteral access sheath 24 (i.e., the calculus 168 are positioned between the raking member 120 and the bladder 110 (FIG. 7)), the raking part 122 of the raking member 120 is moved to the opened or expanded position so that the raking member 120 is in the open or expanded state generally illustrated in FIG. 11. The raking part 122 is expanded after the raking part 122 is positioned on the far side of the calculus 168 (i.e., so that the calculus 168 are positioned between the bladder and the expanded raking part 122). This is identified as position P1 in FIG. 11.

The expansion of the raking part 122 to the open or expanded state as shown in FIG. 11 at least partially occludes the lumen in the ureteral access sheath 24. In the illustrated embodiment, the expanded raking part 122 contacts at least a part of the inner surface of the ureteral access sheath 24 to form a seal with the inner surface of the ureteral access sheath 24. The raking part 122 can be configured to fully occlude the lumen in the ureteral access sheath 24. This can be accomplished by configuring the raking part 12 so that when the raking part 122 is open or expanded, most part of the entire outer periphery of the expanded/open raking part contacts the inner surface of the ureteral access sheath 24.

The raking member 120 with the raking part 122 in the open or expanded condition shown at P1 in FIG. 11 is pulled in the rearward direction (i.e., towards the bladder 110) as generally indicated by the arrow in FIG. 11. This can be accomplished by pulling or otherwise operating the shaft 124. That is, the user or operator can pull on the elongated shaft 24, or the elongated shaft can otherwise be manipulated, to move the enlarged raking part 122 toward the calculus. As the expanded raking part 122 moves in the rearward direction, the expanded raking part 122 rakes the calculus 168. The calculus 168 are thus moved in the rearward direction together with the rearward movement of the expanded raking part 122 as generally illustrated at position P2 in FIG. 11. The expanded raking part 122 continues to be pulled in the rearward direction until the raking member 120 is removed from the ureteral access sheath 24. The rearward or removal movement of the raking member can be accomplished in a variety of ways. For example, the endoscope 40 together with the raking member 120 can be moved rearwardly simultaneously. Alternatively, the endoscope 40 and the raking member 120 can be moved rearwardly in temporal difference (e.g., at first the raking member 120 is pulled back to some extent, then the endoscope 40 is pulled back to some extent, then the raking member 120 is pulled back once again, etc.) In a situation where the length of an elongated shaft 124 is much greater than the length of the instrument channel 42 of the endoscope 40, the operator can remove the endoscope 40 from the ureteral access sheath 24 fully before the rearward and/or removal movement of the raking member 120. As the raking member 120 is removed from the ureteral access sheath 24, so too is the raked-out calculus because the proximal end of the ureteral access sheath 24 is positioned outside the living body.

FIG. 13 illustrates another aspect associated with this embodiment. The lumen in the ureteral access sheath 24 contains liquid (e.g., water, normal saline solution, urine, etc.). Before inserting the ureteral access sheath 24, the urinary tract (i.e. the urethra, the bladder, the ureter, and the kidney) are normally filled with a fluid. This fluid is urine and/or perfusion fluid of the endoscope 40 (e.g., water, normal saline solution). Thus, when the ureteral access sheath 24 is inserted into the urinary tract, fluid flows into (fills) the lumen of the ureteral access sheath 24 naturally. The raking member 120 is configured to create a disturbed flow of this liquid while the expanded raking part 122 is pulled in the rearward direction (i.e., in the direction of the arrow in FIG. 11 to remove the calculus 168. The raking part 122 is configured so that in the expanded or open state illustrated in FIG. 13, the expanded raking part 122 includes a curved, somewhat trumpet-shaped surface 126 that generates a disturbed flow as generally indicated by the arrows in FIG. 13. The disturbed flow produced by the curved surface of the expanded raking part 122 together with the axial rearward movement of the expanded raking part 122 produces the turbulent flow of liquid, and the turbulent flow of liquid tends to lift the calculus from the surface of the ureteral access sheath 24 and also prevents the calculus from settling on the surface of the expanded raking part 22. The disturbed flow is thus beneficial in helping to remove calculus present in the lumen of the ureteral access sheath 24.

FIGS. 12A and 12B depict in a somewhat general fashion one possible configuration of the expandable raking part 122. This embodiment illustrates one example of a frame structure forming part of the expandable raking part 122. A cover is provided over this frame structure to result in the raking part 122 illustrated in FIGS. 10A, 10B, 11 and 13.

Generally speaking, the frame structure forming a part of the expandable raking part 122 includes a plurality of arms each having one end pivotally connected to a common collar 138 fixed in place to a central support 132. A plurality of links 134 are also provided, and one end of each link 134 is connected to a respective arm 130 and the opposite end of each link 134 is connected to a common tubular mount 136. As schematically illustrated in FIG. 12A, the tubular mount 136 is connected to connecting bar 137 to effect adjustment of the tubular mount 136 along the central support 132. The structure shown in FIGS. 12A and 12B is similar to the frame structure of an umbrella. By virtue of this construction, the tubular mount 136 can slide along the central support 132 so that the arms 130 pivot or rotate between a collapsed position where the arms 130 are generally parallel to the central support 132 (i.e., the closed condition or state of the raking member 120 shown in FIG. 10A) and an outwardly expanded position where the arms 130 project outwardly such as shown in FIGS. 12A and 12B (i.e., the open or expanded condition or state of the raking member 120 shown in FIG. 10B).

Figure 14:
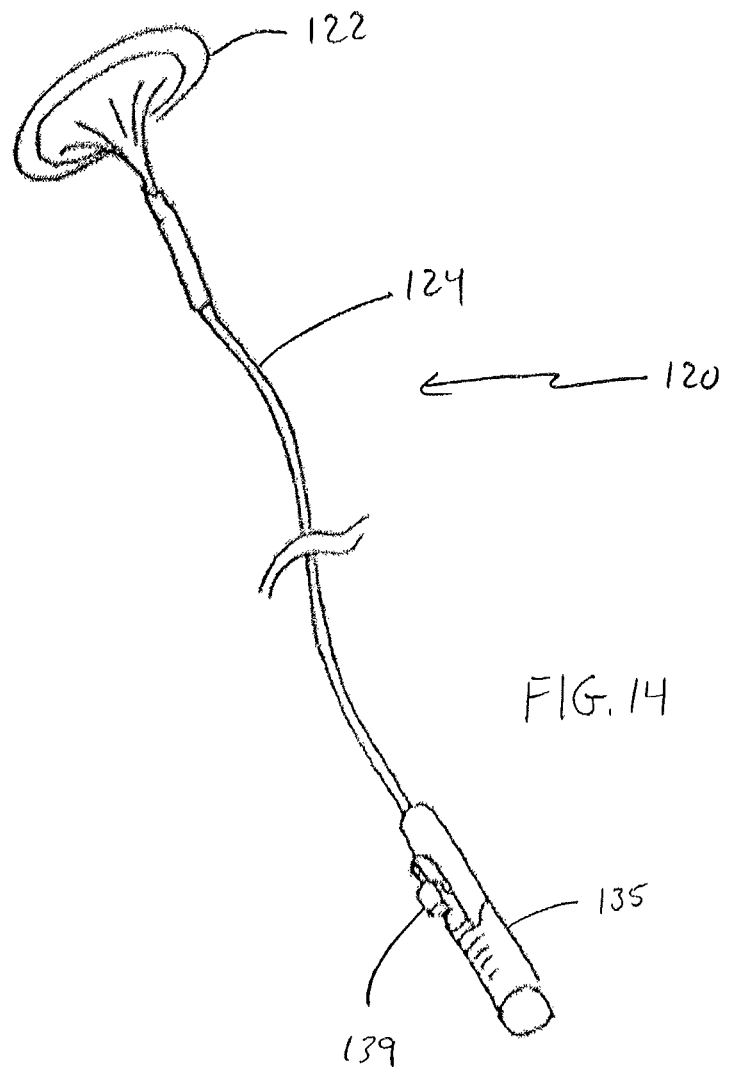
FIG. 14 is a perspective view of the raking member.

FIG. 14 illustrates one example of an overall configuration of the raking member 120. The raking member 120 includes a handle 135 connected to the elongated shaft 124. The raking member 120 also includes an adjustment element 139 that, in this illustrated embodiment, is mounted on the handle 135. The adjustment element 139 can be a manually operable adjustment element in the form of a slide that is manually slidable by the user or operator to open/expand the raking part 122 and close/collapse the raking part 122. The adjustment element 139 is connected to the connecting bar 137 which in turn is connected to the tubular mount 136. Thus, the user can shift the raking part 122 between the closed position shown in FIG. 10A and the open position illustrated in FIGS. 10B and 14 by operating the adjustment element 139 (i.e., by manually sliding the slide). Moving the adjustment element 139 toward the raking part 122 causes the raking part 122 to expand to the position shown in FIGS. 10B and 14, and moving the adjustment element 139 away from the raking part 122 causes the raking part 122 to close or collapse (fold) as illustrated in FIG. 10A.

During use of the raking member 120, the user or operator can hold the handle 135 of the raking member 120 and, when the raking part 122 is in the closed position shown in FIG. 10A, introduce the closed raking part 122 into the instrument channel 42 of the endoscope 40 (ureteroscope). Using the handle 135, the raking member 120 is advanced along the instrument channel 42 of the endoscope 40 so that the raking part 122 is ultimately positioned outside the instrument channel beyond the distal end of the endoscope 40. As described above, after the raking part 122 in the closed position is introduced into the ureteral access sheath 24, the closed raking part 122 is advanced in the direction toward the calculus in the ureteral access sheath 24. The closed raking part 122 is ultimately positioned just beyond the calculus 168 in the ureteral access sheath 24 that are to be removed as indicated by position P1 in FIG. 11. The user or operator can then operate the adjustment element 139 (e.g., by sliding the slide in a forward direction toward the raking part 122) to cause the raking part 122 to shift from the closed state shown in FIG. 10A to the open state illustrated in FIGS. 10B and 14. While still gripping the handle 135, the user or operator can begin pulling the open/expanded raking member 120 in the rearward direction toward the calculus 168 in the ureteral access sheath 24. The rearwardly moving expanded raking part 122 captures and pulls along the calculus 168 in the ureteral access sheath 24. The rearward movement of the expanded raking member 120 is similar to that discussed above.

Figure 15:
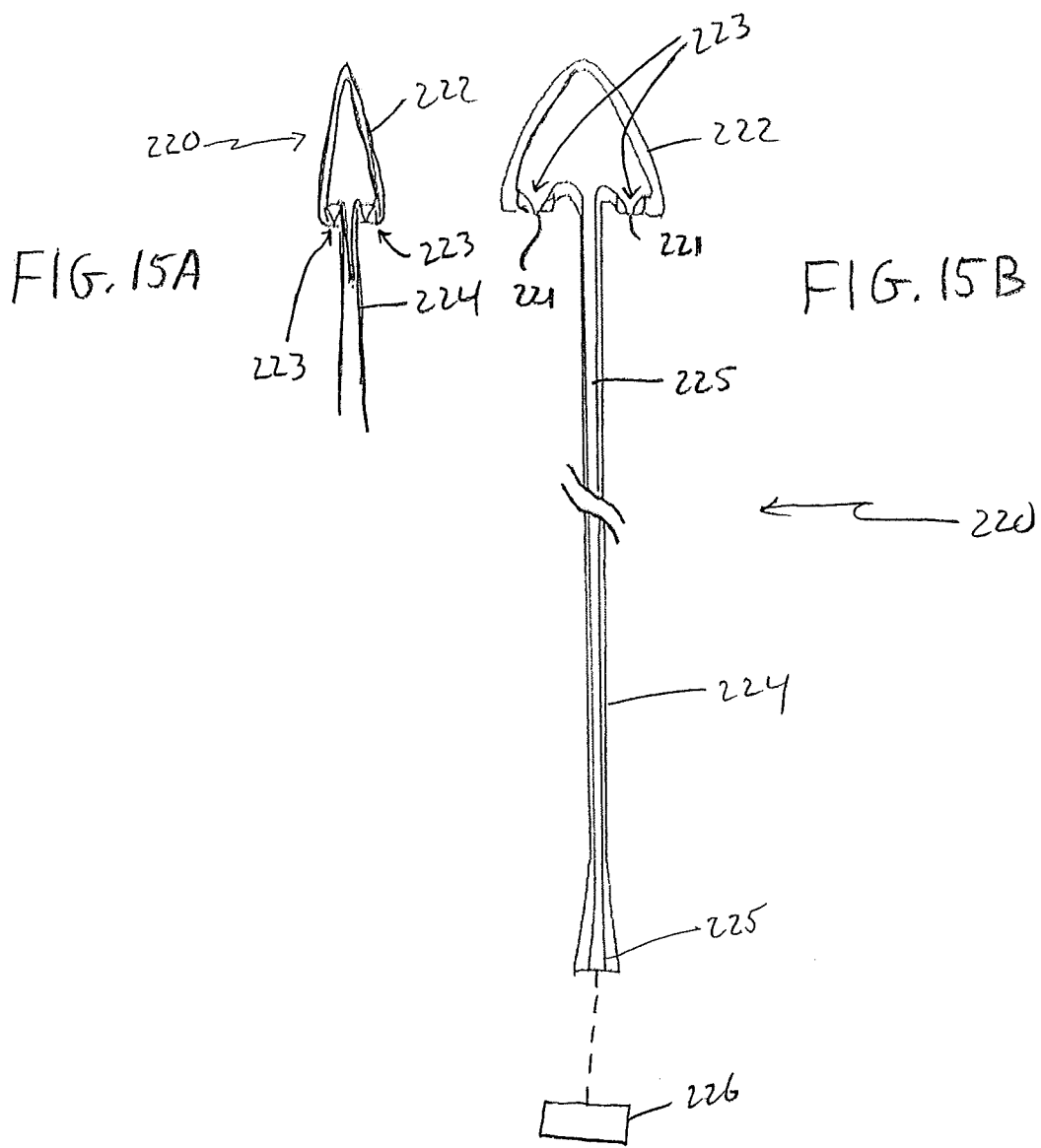
FIG. 15A is a cross-sectional side view of a portion of the raking member with the raking part in the closed or contracted state according to another embodiment.
FIG. 15B is a cross-sectional side view of the raking member with the raking part in the open or expanded state.
Figure 16:
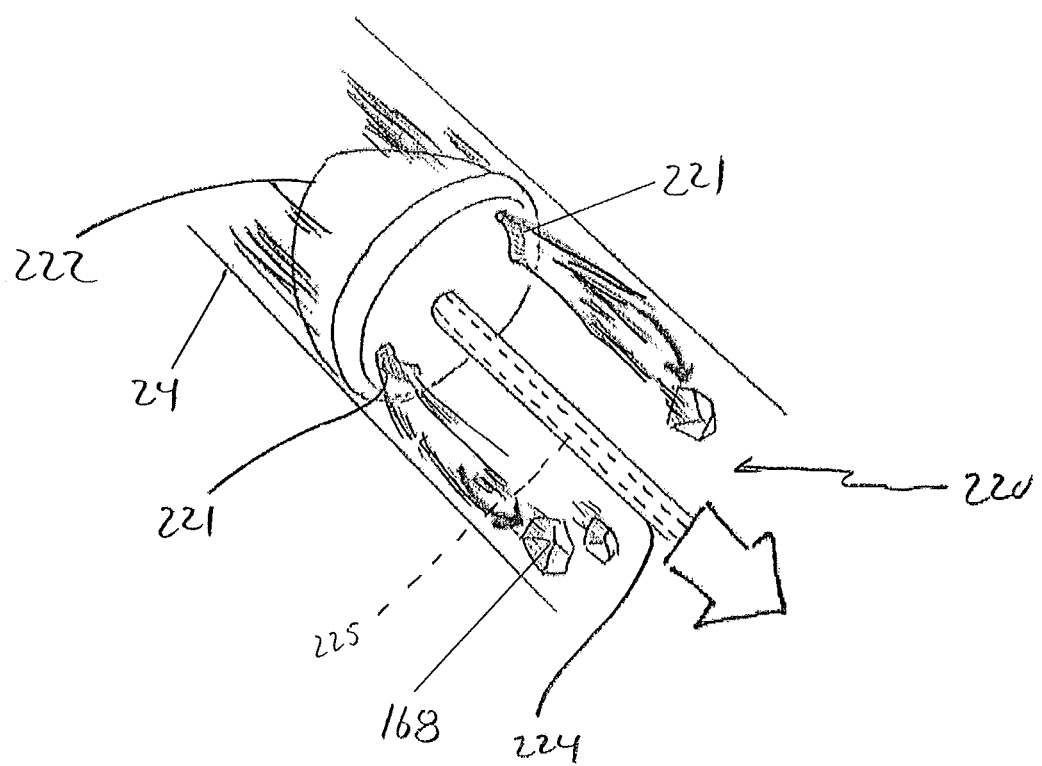
FIG. 16 is a perspective view of the raking member positioned in an ureteral access sheath and illustrating operation aspects of the raking member.

FIGS. 15A, 15B and 16 illustrate another embodiment of the raking member 220. In this embodiment, the raking part 222 is provided with several liquid discharge ports 221 as seen in FIG. 15B and FIG. 16. These liquid discharge ports 221 are connected to the interior of the raking part 222. The interior of the raking part 222 is also in fluid communication with a lumen 225 passing through the elongated shaft 224. This lumen 225 is connected to (in fluid communication with) a source of liquid 226 schematically illustrated in FIG. 15B. The liquid source 226 supplies liquid to the lumen 225 which in turn supplies the liquid to the interior of the raking port 222 and the liquid discharge ports 221. The source of liquid can be a liquid-containing syringe.

The operational procedure involving use of the raking member 220 shown in FIGS. 15A and 15B is as follows. First, the raking member 220 is introduced into the instrument channel of the endoscope 40 (ureteroscope) as described above and is moved to a position just beyond the calculus 168 in the ureteral access sheath 24 that are to be removed in the manner described above. The raking member 220 is moved to a position just beyond the calculus 168 in the ureteral access sheath 24 while the raking part 222 is in the closed position illustrated in FIG. 15A. Next, the raking part 222 is shifted to the open condition in which the raking part 222 is expanded as illustrated in FIGS. 15B and 16. This can be accomplished in the following way.

Each of the liquid discharge ports 221 consists of or includes a check valve (generally identified as 223 in FIG. 15A). In the first step (changing from closed condition shown in FIG. 15A to the open condition shown in FIG. 15B), the check valves 223 of the liquid discharge ports 221 are closed and so the fluid flowing in the lumen 225 can inflate the raking part 222. In the second step (achieving the situation shown in FIG. 16), the check valves 223 of the liquid discharge ports 221 are partially open and so the fluid in the lumen 225 can be exhausted from the inflated raking part 222 and can retain the open (i.e. inflated) condition of the raking part 222.

The expanded raking part 222 is then moved toward the calculus 168 in the ureteral access sheath 24. Liquid is also discharged from the discharge ports 221. According to a preferred operational procedure, the raking member 220 is pulled in the rearward direction towards the calculus 168 while at the same time liquid is discharged from the discharge ports 221. FIG. 16 illustrates the liquid discharged from the discharge ports 221 while the expanded raking part 222 is raking the calculus 168.

The liquid discharged from the discharge ports 221 helps lift the calculus off the interior surface of the ureteral access sheath 24 so that it is easier to rake-out the calculus fragments. In this embodiment, the calculus 168 in the ureteral access sheath 24 are subjected to being raked-out by the raking part 222 and also being washed-out by virtue of the liquid introduced into the ureteral access sheath 24 by way of the discharge ports 221 in the raking part 222.

Figure 17:
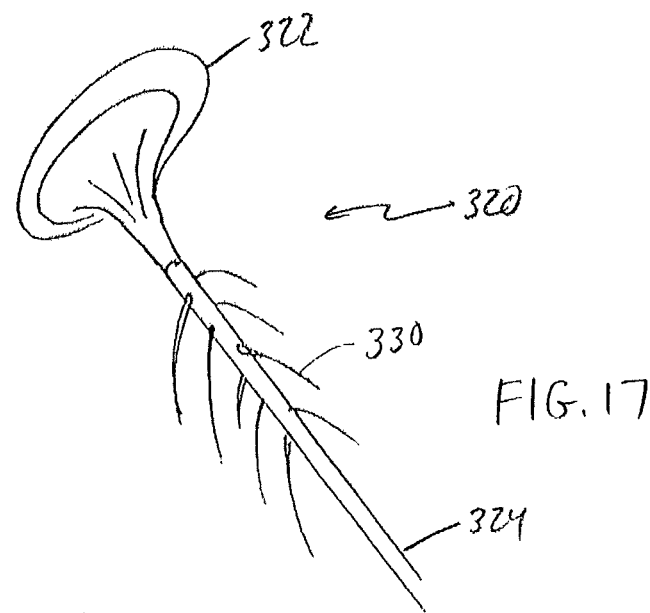
FIG. 17 is a perspective view of another embodiment of the raking member.

FIGS. 17 and 18A-18D illustrate two additional embodiments of the raking member. The embodiment of the raking member 320 illustrated in FIG. 17 is similar to the embodiment illustrated in FIGS. 10A and 10B, except that the raking member 320 also includes a plurality of raking brushes 330. These raking brushes 330 are fixed to the elongated shaft 324 and project outwardly away from the elongated shaft 324. These raking brushes provide an additional mechanism for raking-out or removing calculus in the ureteral access sheath when the expanded raking part 322 is moved in the rearward direction.

Figure 18A:
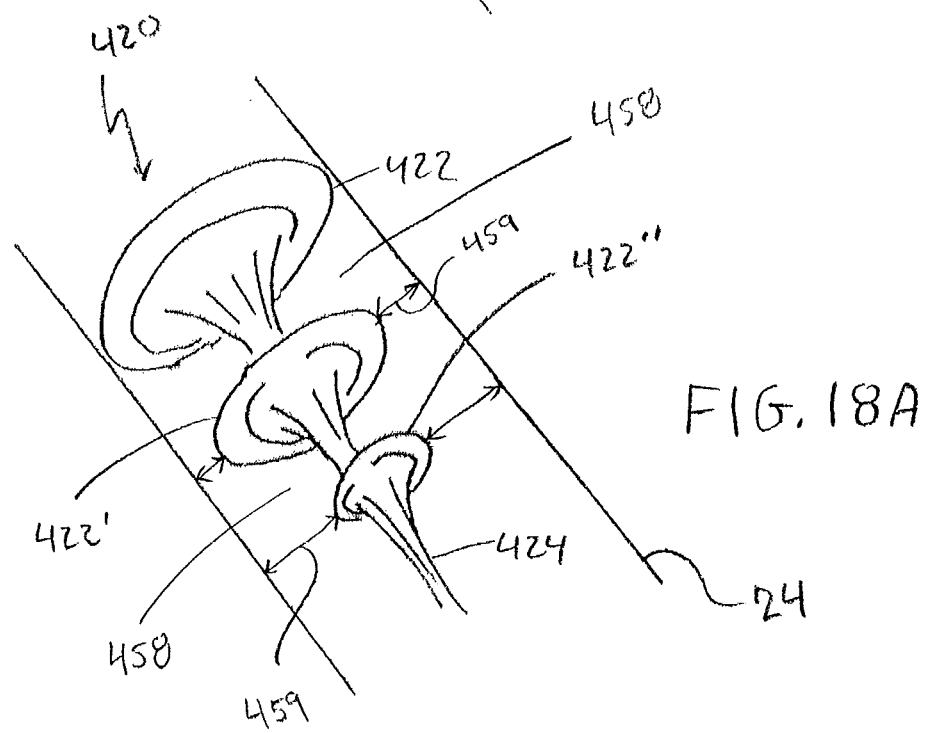

The raking member 420 illustrated in FIGS. 18A-18D is also similar to the embodiment of the raking member described above and illustrated in FIGS. 10A and 10B, except that the embodiment of the raking member 420 in FIGS. 18A-18D includes a plurality of expandable raking parts 422, 422', 422" rather than a single raking part. As shown in FIG. 18A, the expandable raking parts 422, 422', 422" are axially spaced apart from one another along the elongated shaft 424.

In the embodiment illustrated by way of example in FIG. 18A, the distal-most raking part 422 possesses the largest outer size or circumference (outer diameter) when in the expanded state, and then the size or outer dimension of the raking parts in the expanded state become progressively smaller moving away from the distal-most end as shown in FIG. 18A. This decreasing size configuration creates separated retrieval spaces 458 between axially adjacent pairs of the expanded raking parts 422, 422', 422". This decreasing size of the successive expanded raking parts 422, 422', 422" helps prevent the calculus from settling on the surface of the expanded raking parts. This is depicted in FIGS. 18B-18D which show that the calculus are divided automatically into the separated retrieval spaces 458. If the collected calculus becomes a large mass that is collected at one place (a single retrieval space), the pulling force required to pull the retrieved calculus may become excessively large. And if the calculus being retrieved includes relatively larger calculus, the most proximal part of the raking member contacts the calculus first. The illustrated configuration of the raking member 420 is thus able to sort the calculus according to size.

In addition, interspaces 459 exist between the outer periphery of the expanded raking parts 422, 422', 422" and the inner surface of the ureteral access sheath 24. The dimension of the interspace progressively increases from the expanded raking part 422 possessing the larger size circumference to the expanded raking part 422" possessing the smaller size circumference.

It is also to be understood that the embodiments of the raking members 320, 420 shown in FIGS. 17 and 18A-18D can be utilized with features associated with other disclosed embodiments of the raking member. For example, the raking parts 322, 422 of the raking members 320, 420 shown in FIGS. 17 and 18A-18D can be provided with liquid discharge ports such as illustrated in FIGS. 15A, 15B and 16.

The embodiments described above and illustrated in FIGS. 10A-18D involve a raking member that rakes-out calculus in the lumen of the ureteral access sheath. Set forth next is a description of several embodiments of an alternative manner of removing calculus from the interior of the ureteral access sheath. These alternative embodiments utilize a gathering member.

FIGS. 19A, 19B and 20 illustrate one embodiment of a gathering member 550. The gathering member 550 includes an openable and closable gathering part 552 connected to a manipulation wire 554. The gathering member 550 also includes a sheath 556. The manipulation wire 554 passes through the outer sheath 556.

FIG. 19A illustrates the gathering member 550 in a closed or collapsed state in which the gathering part 552 is closed or collapsed and is located in the sheath 556. FIG. 19B illustrates the gathering member 550 in an open or expanded state in which the gathering part 552 is open or expanded and is located outside the sheath 556. The gathering part 552 is shiftable from the closed state in which the gathering part 552 is located inside the sheath 556 to an opened state in which the gathering part 552 is outside the sheath 556 through manipulation or operation of the manipulation wire 554. Similarly, the gathering part 552 is shiftable from the opened state in which the gathering part 552 is outside the sheath 556 to the closed state in which the gathering part 552 is located inside the sheath 556 through manipulation or operation of the manipulation wire 554.

The gathering part 552 can be made of a shape-memory material (e.g., NiTi wire). When made of this material, the gathering part 552 is normally in the open state in the absence of an applied force or load, but is configured to be collapsed to the closed state and positioned inside the sheath 556 as illustrated in FIG. 19A in the presence of an applied force or load (i.e., the force/load that arises when the gathering part 552 is pulled into the sheath 55 through operation of the manipulation wire 554). When the applied force/load is removed (i.e., when the gathering part 552 is moved to a position outside the sheath 556), the gathering part 552 automatically returns to the open or expanded state shown in FIG. 19B.

An example of an operational procedure or method involving the use of the gathering member shown in FIGS. 19A, 19B and 20 is as follows. Initially, the gathering part 552 is in the closed state located inside the sheath 556 as illustrated in FIG. 19A. The gathering member 550 in the state shown in FIG. 19A is introduced into the instrument channel 42 in the endoscope 40 (ureteroscope) which is located in the ureteral access sheath 24 positioned in the lumen in the living body (e.g., the ureter). The gathering member 550 is advanced along the instrument channel 42 and is ultimately introduced into the ureteral access sheath 24. The gathering member 550 in the closed state shown in FIG. 19A is advanced along the ureteral access sheath 24 in a direction towards the calculus to be removed (i.e., the calculus in the ureteral access sheath 24 that are to be removed). The movement of the gathering member 550 is stopped when the distal end of the gathering member 550 is positioned adjacent to but in front of the calculus to be removed (i.e., the gathering member 550 is positioned between the calculus and the bladder). At this time, the gathering member 550 is positioned relative to the fragments of calculus 168 as indicated at position P1 in FIG. 24.

Figure 24:
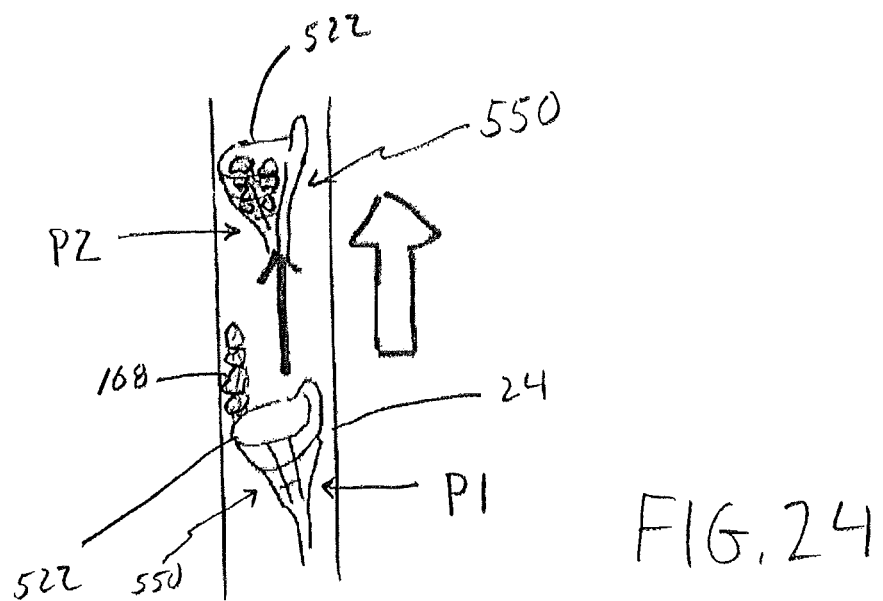
FIG. 24 is a schematic illustration of the gathering member positioned in an ureteral access sheath and movable between two positions.

The gathering member 550 is then moved in the forward direction towards the calculus 168 (i.e., from position P1 toward the position P2 in FIG. 24). This movement of the gathering part 552 causes the calculus 168 in the ureteral access sheath 24 to move into the open gathering part 552. After the calculus 168 are located in the gathering part 552, the gathering member 550 is pulled rearward toward the bladder and ultimately removed from the ureteral access sheath 24. If the calculus are relatively small, the gathering part 552 containing the calculus can be stored (pulled back) into the sheath 556. If the calculus are relatively small, the gathering member 550 whose the gathering part 552 contains the calculus can be pulled back into the instrument channel 42 of the endoscope 40. If the calculus are not relatively small, the gathering part 552 containing the gathered calculus and the endoscope 40 can be simultaneously moved rearwardly. In this latter situation, before pulling back the gathering part 552 containing the calculus, the operator can retract/adjust the size of the inner cavity of the gathering part 552 by withdrawing the manipulation wire 554 to prevent calculus from dropping off (falling out). Sometimes, in the procedure of reducing the size of the inner cavity of the gathering part 552, the withdrawn wire of the gathering part 552 can be used to grasp/keep the calculus effectively.

FIG. 19B illustrates that the gathering part 552 can be provided with a shake-up part 558. This shake-up part 558 is in the form of a projection, or a projecting scoop, that projects distally away from the gathering part 552 over a limited circumferential extent of the gathering part 552. That is, the shake-up part 558 does not extend around the entire circumferential extent of the gathering part 552. As illustrated in FIG. 20, the shake-up part 558 acts as a projecting scoop that can be used to help lift the calculus 168 from the surface of the ureteral access sheath 24 and into the open gathering part 552.

FIGS. 21, 22 and 23 illustrate additional details associated with the gathering member. As illustrated in FIGS. 22 and 23, the gathering member 550 includes a guide part 560 provided with a groove or lumen 562 extending along the length of the guide part 560. The lumen receives a base wire 553 of the gathering part 552 as shown in FIGS. 22 and 23, and allows the base wire 553 (the gathering part 552) to slide along the lumen 562 in the guide part 560. The lumen is configured to include a narrowed opening that prevents the base wire from falling out. Thus, the guide part 560 provides the guide for moving the gathering part between the open and closed position and for guiding the gathering part 552 into the sheath 556.

FIGS. 25-27 illustrates a variation on the direction of the gathering member 550 illustrated in FIGS. 21, 22 and 23. In this illustrated embodiment, the guide part 560 includes a lumen 570 which receives an irrigation tube 572. In the position shown in FIG. 25, the irrigation tube 572 passes through the lumen 570 and extends distally beyond the distal end of the guide part 560. The irrigation tube 572 can be configured in the manner shown in FIG. 25 to include a curve or bend to appropriately direct irrigation liquid discharged from the discharge port or nozzle 574. The irrigation tube 572 is connected to a suitable source of liquid (e.g., water, saline, etc.) The source can be a liquid-filled syringe.

As illustrated in FIG. 25, the irrigation tube 572 is preferably arranged so that the discharge nozzle or port 574 from which the liquid is discharged is angled. In this way, liquid discharged from the nozzle or port is directed at the wall of the ureteral access sheath 24. The liquid discharged from the irrigation port 574 is directed at calculus 168 on the inner surface of the ureteral access sheath 24, causing the calculus 168 to be lifted off of the inner surface of the ureteral access sheath and captured in the open gathering part 552.

The irrigation tube 572 can be made from a shape-memory material. The irrigation tube 572 can thus be accommodated in the lumen 570 of an elongated shaft 524, yet is bent such as in the manner illustrated in FIG. 25 when the distal portion of the irrigation tube 572 is positioned outside the lumen 570. The irrigation tube 572 normally possesses the bent or curved configuration shown in FIG. 25 in the absence of an applied force or load. When a force or load is applied to the irrigation tube 572 such as occurs when the bent or curved portion of the irrigation tube 572 is pulled into the lumen 570, shape or configuration of the irrigation tube 572 changes. When the distal portion of the irrigation tube 572 is outside the lumen 570 as illustrated in FIG. 25, the irrigation tube 572 returns to its normal configuration.

FIG. 25 also illustrates the distal end of the endoscope 40 (ureteroscope). The viewing system defined by the object lens or camera 48 at the distal end of the endoscope 40 can be used to visualize the liquid discharged from the discharge port 574 of the irrigation tube 572 to be appropriately directed at the calculus 168 lying on the inner surface of the ureteral access sheath 24.

Figure 29:
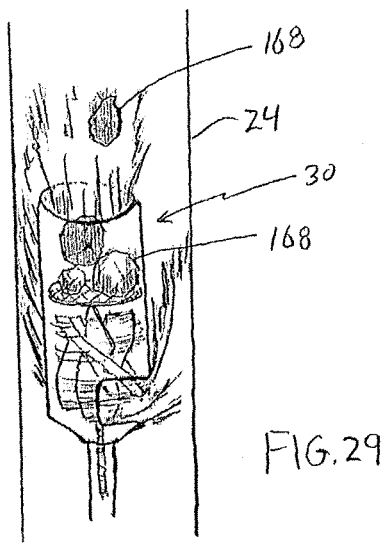
FIG. 29 is a perspective view of the suction member positioned in the ureteral.
Figure 28:
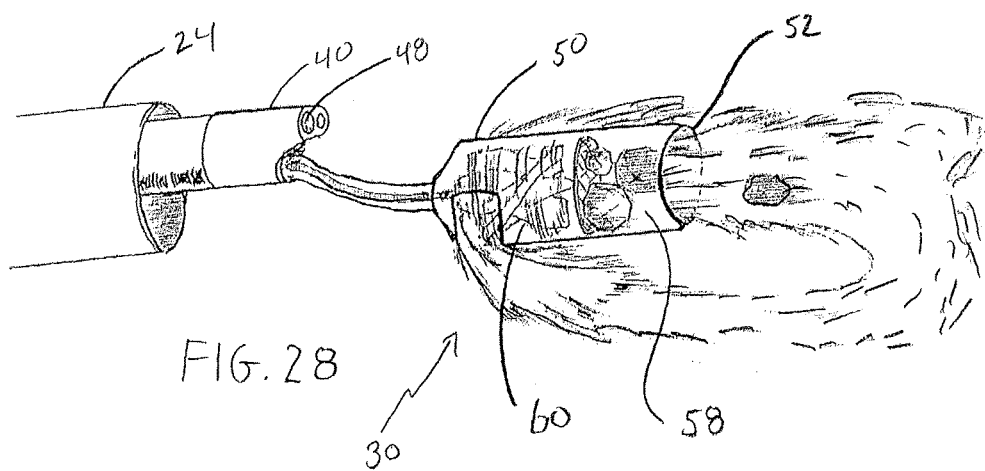
FIG. 28 is a perspective view of a suction member used to retrieve and remove calculus.

A further embodiment of the method or operational procedure for removing calculus from the interior of the ureteral access sheath is illustrated in FIGS. 28 and 29. In this embodiment a retrieving device 30 similar to the retrieving device 30 shown in FIG. 1 is employed. As discussed above in detail, the retrieving device 30 includes a suction head that creates suction to draw calculus into the suction head 50. The calculus in the ureteral access sheath 24 are removed by suction through operation of the suction head 50 as described above. FIG. 28 illustrates the retrieval device 30 positioned outside the ureteral access sheath. This is done simply for ease of illustration and understanding. In actual practice, the retrieval device 30 is located in the ureteral access sheath 24 as illustrated in FIG. 29.

The retrieving device 30 is preferably moved to a position within the ureteral access sheath 24 that is on the bladder side of the calculus 168. This can be accomplished in the same way described above with respect to the raking members and the gathering members. When the suction head 50 is positioned adjacent to, and on the bladder side of, the calculus 168 (i.e., the suction head 50 is preferably not moved past the calculus 168), the suction head 50 is operated so that the impeller in the housing of the suction head 50 rotates and creates suction that draws the calculus 168 located in the ureteral access sheath 24 into the suction head housing. After the suction head 50 is operational (i.e., after the impeller in the suction head housing is rotating and creating suction), the suction head is preferably moved forward toward the calculus 168. The operation of the suction housing creates convection in the ureteral access sheath 24 that helps lift the calculus from the surface of the ureteral access sheath 24, thus facilitating drawing the calculus 168 into the interior of the housing of the suction head 50.

Through operation of the suction head 50 in the manner described above, calculus 168 inside the ureteral access sheath 24 are drawn into the interior of the housing of the suction head 50. After the calculus 168 have been captured or retrieved and are held in the housing of the suction head 50, the endoscope 40, together with the suction head holding the retrieved calculus fragments, can be pulled rearwardly to remove the endoscope and the suction head from the ureteral access sheath 24, and ultimately removed from the living body. It is possible to utilize the viewing system associated with the endoscope 40 (i.e., the lens or camera 48) during operation of the suction head 50 to capture or retrieve the calculus in the interior of the ureteral access sheath 24. This endoscope viewing system can also be used in each of the embodiments of the raking member and gathering member described above.

The retrieval of the calculus and the retention of the calculus during movement of the suction head 50 can be accomplished by controlling various operational parameters of the suction head 50. These operational parameters include the rotation operation of the impeller 60 (ON/OFF) and the rotation speed of the impeller 60. That is, by varying the rotation operation and the rotation speed of the impeller 60, it is possible to control the retrieval and the retention of the calculus.

During retrieval of the calculus, the impeller 60 is preferably rotated (i.e., the rotational operation is ON), is rotated at a relatively high speed (e.g., 15,000 rpm-20,000 rpm), and is rotated in the overspin direction intended to create suction in the suction head 50. The calculus is thus drawn toward the open distal end 52 of the suction head 50 and enter the retrieval space 58 as shown in FIGS. 28 and 29.

After the calculus has been retrieved, it is necessary to retain the retrieved calculus in the retrieval space 58 of the suction head 50 while moving the suction head 50 to remove the retrieving device 30 from the ureteral access sheath 24. To retain the retrieved calculus, the driving device 28 continues to operate (i.e., the rotational operation is ON) so that the impeller 60 continues rotating. The rotation direction of the impeller 60 is the same as the rotation direction of the impeller during retrieval of the calculus. In addition, the rotation speed of the impeller 60 can be the same relatively high speed as the rotation speed of the impeller 60 during retrieval of the calculus/calculi, or can be a slightly slower rotation speed (e.g., 12,000 rpm-15,000 rpm).

The retrieving device 30 has sufficient space in the retrieval space 58 to retrieve the fragments of calculus. In addition, created suction flow can pack the retrieved fragments of calculus closely in the retrieval space 58. That is why, after the calculus has been retrieved from the ureteral access sheath 24, the operator can choose whether to remove the retrieving device 30 from the ureteral access sheath 24 or to advance the retrieving device 30 in the ureteral access sheath 24 toward the kidney for continuing the retrieving in a pathological area (i.e., the ureter, the renal pelvis and/or the renal calix) in the living body. To retain the retrieved calculus while moving the suction head 50 to move the retrieving device 30 toward the kidney, the driving device 28 continues to operate (i.e., the rotational operation is ON) so that the impeller 60 continues rotating. The rotation direction of the impeller 60 is the same as the rotation direction of the impeller during retrieval of the calculus. In addition, the rotation speed of the impeller 60 can be the same relatively high speed as the rotation speed of the impeller 60 during retrieval of the calculus/calculi, or can be a slightly slower rotation speed (e.g., 12,000 rpm-15,000 rpm).

The description above describes ways of positioning the raking member, gathering member and suction member at the desired place in the lumen in the living body to remove the calculus. For example, it is possible to introduce the raking member, gathering member and/or suction member into the instrument channel 42 in the endoscope 40 while the endoscope is outside the living body, introducing the endoscope 40 (the raking member, gathering member and/or suction member) into the ureteral access sheath 24 that is positioned in the lumen of the living body (the endoscope 40 is introduced into the proximal end of the ureteral access sheath 24, which proximal end of the ureteral access sheath 24 is positioned outside the living body), advancing the endoscope 40 (with the raking member, gathering member and/or suction member) along the ureteral access sheath 24 and to the location in the lumen in the living body at which is located the calculus to be retrieved. Alternatively, it is possible, if the size of the raking member, gathering member and/or suction member permits, to introduce the endoscope 40 into the ureteral access sheath 24 that is positioned in the lumen of the living body (the endoscope 40 is introduced into the proximal end of the ureteral access sheath 24, which proximal end of the ureteral access sheath 24 is positioned outside the living body), introducing the raking member, gathering member and/or suction member into the instrument channel 42 of the endoscope 40 while the endoscope 40 is in the ureteral access sheath 24, advancing the raking member, gathering member and/or suction member along the instrument channel so that the raking member, gathering member and/or suction member enters the ureteral access sheath 24 and is advanced to the location in the lumen in the living body at which is located the calculus to be retrieved.

Set forth above is a description of various embodiments of methods or operational procedures, and devices, for removing calculus from the ureteral access sheath 24. The raking and/or washing out procedures are quite advantageous because the efficacy of the removal operation is not significantly impacted by small-sized because the small-sized calculus can be rather easily raked-out and/or washed-out. Similarly, the gathering embodiments are not negatively affected in a significant way when removing small-sized calculus because the efficacy of lifting calculus via the shake-up part 558 and/or utilizing irrigation from the discharge part or nozzle 574 are not influenced by small-sized calculus because the small-sized calculus can be fairly easily gathered and/or irrigated. Further, being able to adjust the reticulation of the gathering part 552 is useful to prevent small calculus from dropping off, and the efficacy of suction is not influenced by the size of the calculus because rather small-sized calculus are easy to be drawn in.

The detailed description above describes devices and methods for removing calculus from a ureteral access sheath. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A method comprising:
removing from a lumen in an ureteral access sheath a calculus retrieving device used to retrieve calculus in a living body, the living body including a ureter extending between a bladder in the living body and a kidney in the living body, at least a portion of the ureteral access sheath being located in the ureter, the calculus retrieving device being removed from the lumen of the ureteral access sheath while the ureteral access sheath is positioned in the living body, with calculus located in the lumen in the ureteral access sheath following removal of the calculus retrieving device from the ureteral access sheath;
introducing a gathering member into the lumen in the ureteral access sheath, the gathering member possessing a distal end;
moving the gathering member along the lumen in the ureteral access sheath in a forward direction toward the calculus so that the gathering member approaches the calculus;
stopping the movement of the gathering member in the forward direction to position the gathering member between the proximal end of the ureteral access sheath and the calculus;
expanding the gathering member while the gathering member is positioned between the proximal end of the ureteral access sheath and the calculus, the expansion of the gathering member opening a gathering part of the gathering member so that the gathering part is open to receive the calculus;
introducing the calculus into the open gathering part of the gathering member;
moving the gathering member with the calculus enclosed in the gathering part of the gathering member along the lumen in the ureteral access sheath in a direction toward the proximal end of the ureteral access sheath; and
removing the gathering member as well as the calculus enclosed in the gathering part of the gathering member from the lumen of the ureteral access sheath.

2. The method according to claim 1, wherein the gathering member is introduced into the lumen in the ureteral access sheath by first inserting the gathering member into a channel in an ureteroscope.

3. The method according to claim 1, wherein the introduction of the calculus into the gathering part of the gathering member comprises moving the gathering member along the lumen in the ureteral access sheath in the forward direction after expanding the gathering member.

4. The method according to claim 1, wherein the expansion of the gathering member includes expanding the gathering member into contact with an inner surface of the ureteral access sheath.

5. The method according to claim 1, further comprising generating a disturbed flow in the lumen of the ureteral access sheath while the gathering member is positioned between the proximal end of the ureteral access sheath and the calculus.

6. The method according to claim 1, further comprising discharging a liquid into the ureteral access sheath to help introduce the calculus into the gathering part of the gathering member.

7. The method according to claim 6, wherein the liquid is discharged from a port that is directed toward the calculus so that the liquid is ejected from the port at the calculus.

8. The method according to claim 1, wherein the gathering part of the gathering member includes a forwardly projecting shake-up part that extends along only a limited circumferential extent of the gathering part, further comprising using the forwardly projecting shake-up part to lift the calculus from an inner surface of the ureteral access sheath.

9. The method according to claim 1, wherein the gathering part of the gathering member is collapsed to close the gathering part before moving the gathering member with the calculus enclosed in the gathering part of the gathering member along the lumen in the ureteral access sheath in the direction toward the proximal end of the ureteral access sheath.

10. The method according to claim 1, wherein the gathering member includes a gathering part, further comprising retracting the gathering part of the gathering member to retain the calculus before moving the gathering member with the calculus enclosed in the gathering part of the gathering member along the lumen in the ureteral access sheath in the direction toward the proximal end of the ureteral access sheath.

11. A method comprising:
introducing a gathering part into a lumen in an ureteral access sheath in which is located calculus, the gathering part being introduced into the ureteral access sheath while at least a part of the ureteral access sheath is located in an ureter in a living body, the gathering part being expandable to an open state in which the gathering part is open to receive the calculus;
moving the gathering part along the lumen in the ureteral access sheath in a forward direction toward the calculus in the lumen of the ureteral access sheath and toward a distal end of the ureteral access sheath;
stopping movement of the gathering part in the forward direction in the lumen of the ureteral access sheath to position the gathering part adjacent the calculus so that the calculus is positioned between the distal end of the ureteral access sheath and the gathering part;
expanding the gathering part, while the gathering part is positioned adjacent the calculus, to the open state in which the gathering part is open to receive the calculus;
introducing the calculus into the gathering part of the gathering member; and
removing the gathering part as well as the calculus in the gathering part from the lumen of the ureteral access sheath.

12. The method according to claim 11, wherein the gathering part is introduced into the lumen in the ureteral access sheath by first inserting the gathering part into a channel in an ureteroscope.

13. The method according to claim 11, wherein the receiving part of the gathering member includes a forwardly projecting shake-up part that extends along only a limited circumferential extent of the gathering part, the method further comprising using the forwardly projecting shake-up part to lift the calculus from an inner surface of the ureteral access sheath.

14. The method according to claim 11, wherein the expansion of the gathering part includes expanding the gathering part into contact with an inner surface of the ureteral access sheath.

15. The method according to claim 11, further comprising generating a disturbed flow in the lumen of the ureteral access sheath while the gathering part is positioned so that the calculus is located between the gathering part and the distal end of the ureteral access sheath.

16. The method according to claim 11, further comprising discharging a liquid into the ureteral access sheath to help introduce the calculus into the receiving part of the gathering member.

17. The method according to claim 16, wherein the liquid is discharged from a port that is directed toward the calculus so that the liquid is ejected from the port at the calculus.

18. The method according to claim 11, wherein the gathering part is connected to a distal end of an elongated shaft, and the elongated shaft is operated to move the gathering part.

* * * * *